US011542247B2

(12) United States Patent
Angibaud et al.

(10) Patent No.: US 11,542,247 B2
(45) Date of Patent: Jan. 3, 2023

(54) BI-HETEROARYL SUBSTITUTE 1,4-BENZODIAZEPINES AND USES THEREOF FOR THE TREATMENT OF CANCER

(71) Applicant: Janssen Pharmaceutica NV, Beerse (BE)

(72) Inventors: Patrick Rene Angibaud, Saint Pierre d'Autils (FR); Diego Fernando Domenico Broggini, Zurich (CH); Filip Albert C Cuyckens, Aartselaar (BE); Steven Anna Hostyn, Hove (BE); Russell Mark Jones, Binningen (CH); Olivier Alexis Georges Querolle, Saint Vigor (FR); Wim Vermeulen, Vosselaar (BE)

(73) Assignee: Janssen Pharmaceutica NV, Beerse (BE)

( * ) Notice: Subject to any disclaimer, the term of this patent is extended or adjusted under 35 U.S.C. 154(b) by 620 days.

(21) Appl. No.: 15/762,552

(22) PCT Filed: Sep. 22, 2016

(86) PCT No.: PCT/EP2016/072501
§ 371 (c)(1),
(2) Date: Mar. 22, 2018

(87) PCT Pub. No.: WO2017/050865
PCT Pub. Date: Mar. 30, 2017

(65) Prior Publication Data
US 2020/0255401 A1  Aug. 13, 2020

(30) Foreign Application Priority Data
Sep. 23, 2015  (EP) .................................... 15186478

(51) Int. Cl.
*C07D 401/14*  (2006.01)
*A61P 35/00*  (2006.01)
*C07D 471/04*  (2006.01)
*C07D 403/14*  (2006.01)

(52) U.S. Cl.
CPC ............ *C07D 401/14* (2013.01); *A61P 35/00* (2018.01); *C07D 403/14* (2013.01); *C07D 471/04* (2013.01)

(58) Field of Classification Search
CPC .. C07D 401/14; C07D 403/14; C07D 471/04; A61P 35/00
See application file for complete search history.

(56) References Cited

U.S. PATENT DOCUMENTS 2,940,972 A   6/1960  Roch
4,166,117 A   8/1979  Vincent et al.
4,666,828 A   5/1987  Gusella
4,683,202 A   7/1987  Mullis
4,801,531 A   1/1989  Frossard
5,192,659 A   3/1993  Simons
5,272,057 A   12/1993 Smulson et al.
5,700,823 A   12/1997 Hirth et al.
5,882,864 A   3/1999  An et al.
6,218,529 B1  4/2001  An et al.
6,271,231 B1  8/2001  Bergstrand et al.
6,331,555 B1  12/2001 Hirth et al.
7,432,279 B2  10/2008 Green et al.
8,895,601 B2  11/2014 Murray et al.
9,145,367 B2  9/2015  Tazi et al.
9,221,804 B2  12/2015 Leonard et al.
9,290,478 B2  3/2016  Saxty et al.
9,303,029 B2  4/2016  Woodhead et al.
9,303,030 B2  4/2016  Angibaud et al.
9,309,241 B2  4/2016  Angibaud et al.
9,309,242 B2  4/2016  Berdini et al.
9,439,896 B2  9/2016  Berdini et al.
9,447,098 B2  9/2016  Saxty et al.
9,464,071 B2  10/2016 Saxty et al.
9,493,426 B2  11/2016 Angibaud et al.
9,527,844 B2  12/2016 Angibaud et al.
9,737,544 B2  8/2017  Angibaud et al.
9,757,364 B2  9/2017  Obringer et al.
9,850,228 B2  12/2017 Saxty et al.
9,856,236 B2  1/2018  Saxty et al.
10,039,759 B2 8/2018  Berdini et al.
10,045,982 B2 8/2018  Berdini et al.
(Continued)

FOREIGN PATENT DOCUMENTS

CA  2524525 A1  12/2004
CA  2524948 A1  12/2004
(Continued)

OTHER PUBLICATIONS

Zhenkun Ma et al., Novel Erythromycin Derivatives with Aryl Groups Tethered to the C-6 Position Are Potent Protein Synthesis Inhibitors and Active against Multidrug-Resistant Respiratory Pathogens, J. Med. Chem. 2001, 44, 4137-4156 (Year: 2001).*
Mayo Clinic webpage for stomach cancer; accessed Feb. 7, 2021 (Year: 2021).*
March, J., "Advanced Organic Chemistry—Reactions, Mechanisms, and Structure", John Wiley & Sons, Inc., (1992), 4th Edition, A Wiley-Interscience Publication, see Table of Contents.
Angerer, R.C., et al., "Demonstraton of Tissue-Specific Gene Expression by in Situ Hybridization", Methods in Enzymology, (1987), vol. 152, p. 649.
Bartlett, J.M.S., "Fluorescence In Situ Hybridization", Methods in Molecular Methods, (2004), vol. 97, pp. 77-88.
(Continued)

*Primary Examiner* — Kortney L. Klinkel
*Assistant Examiner* — Jason Deck
(74) *Attorney, Agent, or Firm* — BakerHostetler

(57) ABSTRACT

The invention relates to new quinoline, pyridopyrazine, naphthyridine and quinazolinone derivative compounds, to pharmaceutical compositions comprising said compounds, to processes for the preparation of said compounds and to the use of said compounds in the treatment of diseases, e.g. cancer.

25 Claims, No Drawings

(56) References Cited

U.S. PATENT DOCUMENTS

| | | |
|---|---|---|
| 10,052,320 B2 | 8/2018 | Woodhead et al. |
| 10,085,982 B2 | 10/2018 | Jovcheva et al. |
| 2003/0207886 A1 | 11/2003 | Plucker et al. |
| 2004/0236084 A1 | 11/2004 | Biwersi et al. |
| 2005/0075325 A1 | 4/2005 | Burnett et al. |
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0156617 A1 | 6/2009 | Northrup |
| 2009/0221591 A1 | 9/2009 | Hartmann et al. |
| 2009/0234347 A1 | 9/2009 | Treat et al. |
| 2009/0263397 A1 | 10/2009 | Buck et al. |
| 2010/0216767 A1 | 8/2010 | Aikawa et al. |
| 2010/0228026 A1 | 9/2010 | Yoshida et al. |
| 2010/0234347 A1 | 9/2010 | Dollinger et al. |
| 2010/0292190 A1 | 11/2010 | Chaplin et al. |
| 2010/0296236 A1 | 11/2010 | Schuette |
| 2011/0123545 A1 | 5/2011 | Marsh et al. |
| 2012/0302572 A1 | 11/2012 | Kan et al. |
| 2013/0072457 A1 | 3/2013 | Murray et al. |
| 2013/0267525 A1 | 10/2013 | Saxty et al. |
| 2014/0037642 A1 | 2/2014 | Lu et al. |
| 2014/0288053 A1 | 9/2014 | Berdini et al. |
| 2014/0296236 A1 | 10/2014 | Berdini et al. |
| 2015/0031669 A1 | 1/2015 | Woodhead et al. |
| 2015/0031703 A1 | 1/2015 | Suzuki et al. |
| 2015/0057293 A1 | 2/2015 | Angibaud et al. |
| 2015/0105368 A1 | 4/2015 | Saxty et al. |
| 2015/0203589 A1 | 7/2015 | Iavarone et al. |
| 2015/0239883 A1 | 8/2015 | Angibaud et al. |
| 2015/0291589 A1 | 10/2015 | Saxty et al. |
| 2016/0031856 A1 | 2/2016 | Saxty et al. |
| 2016/0075666 A1 | 3/2016 | Angibaud et al. |
| 2016/0108034 A1 | 4/2016 | Angibaud et al. |
| 2016/0213677 A1 | 7/2016 | Angibaud et al. |
| 2016/0220564 A1 | 8/2016 | Woodhead et al. |
| 2016/0235744 A1 | 8/2016 | Berdini et al. |
| 2016/0287699 A1 | 10/2016 | Karkera et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0105978 A1 | 4/2017 | Obringer et al. |
| 2017/0119763 A1 | 5/2017 | Jovcheva et al. |
| 2018/0021332 A1 | 1/2018 | Broggini |
| 2018/0127397 A1 | 5/2018 | Saxty et al. |
| 2018/0296558 A1 | 10/2018 | Perera et al. |

FOREIGN PATENT DOCUMENTS

| | | |
|---|---|---|
| CN | 1128496 A | 8/1996 |
| CN | 102036963 A | 4/2011 |
| EP | 0 548 934 A1 | 6/1993 |
| EP | 0544445 A2 | 6/1993 |
| EP | 1001946 A1 | 5/2000 |
| EP | 1990342 A1 | 11/2008 |
| EP | 2332939 A1 | 6/2011 |
| EP | 2650293 A1 | 10/2013 |
| JP | 2003-213463 A | 7/2003 |
| JP | 2006-516561 A | 7/2006 |
| JP | 2008-530030 A | 8/2008 |
| JP | 2008-540535 A | 11/2008 |
| JP | 2010-514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 98/54157 A1 | 12/1998 |
| WO | 99/09845 A1 | 3/1999 |
| WO | 99/17759 A2 | 4/1999 |
| WO | WO 2000/042026 A1 | 7/2000 |
| WO | WO 2000/055153 A1 | 9/2000 |
| WO | 01/19825 A1 | 3/2001 |
| WO | WO 2001/068047 A2 | 9/2001 |
| WO | 02/76985 A1 | 10/2002 |
| WO | WO 2002/096873 A1 | 12/2002 |
| WO | 03/51833 A2 | 6/2003 |
| WO | 03/55491 A1 | 7/2003 |
| WO | WO 2003/076416 A1 | 9/2003 |
| WO | 03/86394 | 10/2003 |
| WO | 2004/006355 A2 | 1/2004 |
| WO | WO 2004/030635 A2 | 4/2004 |
| WO | 2004/043950 A1 | 5/2004 |
| WO | 2004/056822 A1 | 7/2004 |
| WO | 2004/065378 A1 | 8/2004 |
| WO | WO 2004/098494 A2 | 11/2004 |
| WO | 2004/110350 A2 | 12/2004 |
| WO | WO 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005/054231 A1 | 6/2005 |
| WO | 2005/061463 A1 | 7/2005 |
| WO | 2006/040036 A1 | 4/2006 |
| WO | 2006/040052 A1 | 4/2006 |
| WO | 2006/040568 A1 | 4/2006 |
| WO | 2006/066361 A1 | 6/2006 |
| WO | 2006/084338 A1 | 8/2006 |
| WO | WO 2006/092430 A1 | 9/2006 |
| WO | 2006/124354 A2 | 11/2006 |
| WO | WO 2007/003419 A1 | 1/2007 |
| WO | 2007/023186 A1 | 3/2007 |
| WO | 2007/054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2007/140222 A2 | 12/2007 |
| WO | WO 2008/003702 A2 | 1/2008 |
| WO | 2008/076278 A2 | 6/2008 |
| WO | 2008/078091 A1 | 7/2008 |
| WO | 2008/079988 A2 | 7/2008 |
| WO | 2008/080015 A2 | 7/2008 |
| WO | 2008/082198 A1 | 7/2008 |
| WO | 2008/138878 A2 | 11/2008 |
| WO | WO 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/020990 A1 | 2/2009 |
| WO | 2009/021083 A1 | 2/2009 |
| WO | 2009/064835 A1 | 5/2009 |
| WO | 2009/137378 A2 | 11/2009 |
| WO | WO 2009/141386 A1 | 11/2009 |
| WO | 2010/059771 A1 | 5/2010 |
| WO | 2010/084152 A1 | 7/2010 |
| WO | 2010/088177 A1 | 8/2010 |
| WO | 2010/129570 A1 | 11/2010 |
| WO | WO 2011/026579 A1 | 3/2011 |
| WO | WO 2011/028947 A2 | 3/2011 |
| WO | WO 2011/047129 A1 | 4/2011 |
| WO | 2011/064250 A1 | 6/2011 |
| WO | 2011/126903 A2 | 10/2011 |
| WO | 2011/146591 A1 | 11/2011 |
| WO | WO 2011/135376 A1 | 11/2011 |
| WO | 2011/149937 A1 | 12/2011 |
| WO | WO 2012/073017 A1 | 6/2012 |
| WO | 2012/104776 A1 | 8/2012 |
| WO | 2012/118492 A1 | 9/2012 |
| WO | 2012/148540 A1 | 11/2012 |
| WO | WO 2012/154760 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061305 A1 | 5/2013 |

(56) References Cited

FOREIGN PATENT DOCUMENTS

| WO | 2013/063217 A1 | 5/2013 | |
|---|---|---|---|
| WO | WO 2013/061074 A1 | 5/2013 | |
| WO | WO 2013/061077 A1 | 5/2013 | |
| WO | WO 2013/061080 A1 | 5/2013 | |
| WO | WO 2013/061081 A1 | 5/2013 | |
| WO | WO 2013/179033 A1 | 12/2013 | |
| WO | WO 2013/179034 A1 | 12/2013 | |
| WO | 2014/113729 A2 | 7/2014 | |
| WO | WO 2014/174307 A1 | 10/2014 | |
| WO | 2015/017607 A2 | 2/2015 | |
| WO | WO 2015/144803 A1 | 10/2015 | |
| WO | WO 2015/144804 A1 | 10/2015 | |
| WO | WO 2015/144808 A1 | 10/2015 | |
| WO | WO-2015144804 A1 * | 10/2015 | ......... A61K 31/4985 |
| WO | 2016/128411 A1 | 8/2016 | |
| WO | 2016/134234 A1 | 8/2016 | |
| WO | 2016/161239 A1 | 10/2016 | |
| WO | 2017/140222 A1 | 8/2017 | |

OTHER PUBLICATIONS

Berge, S.M., et al., "Pharmaceutical Salts", J. Pharm. Sci., (1977), vol. 66, No. 1, pp. 1-19.
Cahn, R.S., et al., "Specification of Molecular Chirality", Angew. Chem. Internat. Edit., (1966), vol. 5, No. 4, pp. 385-415.
Deady, L.W., "Ring Nitrogen Oxidation of Amino Substituted Nitrogen Heterocycles With m-Chloroperbenzoic Acid", Synthetic Communications, (1977), vol. 7, No. 8, pp. 509-514.
Deprimo, S.E., et al., "Expression profiling of blood samples from an SU5416 Phase III metastatic colorectal cancer clinical trial: a novel strategy for biomarker identification", BMC Cancer, (2003), vol. 3, No. 3, pp. 1-12.
Innis, M.A., et al., "PCR Protocols: A Guide to Methods and Applications", Academic Press, Inc., (1990), Table of Contents.
Knights, V., et al., "De-regulated FGF receptors as therapeutic targets in cancer", Pharmacology & Therapeutics, (2010), vol. 125, No. 1, pp. 105-117.
Korc, M., et al., "The Role of Fibroblast Growth Factors in Tumor Growth", Current Cancer Drug, (2009), vol. 9, No. 5, pp. 639-651.
Sambrook, J., et al., "Molecular Cloning: A Laboratory Manual", Cold Spring Harbor Laboratory Press, (2001), Table of Contents.
Stahl, P.H., et al., "Pharmaceutical Salts: Properties, Selection, and Use: $2^{nd}$ Revised Edition", Chemistry International, (2011), Summary Page.
International Search Report PCT/EP2016/072501 dated Dec. 20, 2016.
Ausubel, F.M. et al., eds. (2004) Current Protocols in Molecular Biology.
"Himicheskajajenciklopedija" tom 4, str. 990-993, izdatefstvo "Sovetskajajencklopedija", Moskva, 1988 (In English: Chemical Encyclopedia, vol. 4, pp. 990-993, Publishing House "Soviet encyclopedia", Moscow, 1988).
"Himicheskajajenciklopedija" tom. 1, stranicy 242-243, izdatefstvo "Sovetskajajencklopedija", Moskva, 1988 (In English: Chemical Encyclopedia (thesaurus), vol. 1, pp. 242-243, publishing house "Soviet encyclopedia", Moscow, 1988).
Adcock, J., et al., Diversity oriented synthesis: substitution at C5 in unreactive pyrimidines by Claisen rearrangement and reactivity in nucleophilic substitution at C2 and C4 in pteridines and pyrido[2,3-(7]pyrimidines, Tetrahedron, vol. 67, pp. 3226-3237 (2011).
Arai et al., "Fibroblast Growth Factor Receptor 2 Tyrosine Kinase Fusions Define a Unique Molecular Subtype of Cholangiocarcinoma," Hepatology, Apr. 2014, vol. 59, No. 4, pp. 1427-1434.
Avendano, C., et al., "Drugs That Inhibit Signalling Pathways for Tumor Cell Growth and Proliferation", Medicinal Chemistry of Anticancer Drugs, pp. 251-305 (2008).
Bahleda et al., "Phase 1 Study of JNJ-42756493, a Pan-Fibroblast Growth Factor Receptor (FGFR) Inhibitor, in Patients with Advanced Solid Tumors," Journal of Clinical Oncology, May 2014, vol. 32, No. 15, pp. 2501-2501.

Berge, Stephen M. et al. "Pharmaceutical Salts", Journal of Pharmaceutical Sciences, vol. 66, No. 1, 1977, pp. 1-19.
Bronte et al., "Nintedanib in NSCLC: Evidence to Date and Place in Therapy," Therapeutic Advances in Medical Oncology, 2016, vol. 8[3], pp. 188-197.
Carneiro, B.A., et al., Emerging therapeutic targets in bladder cancer, Cancer Treatment Reviews, vol. 41, No. 2, pp. 170-178 (2015).
Cecil Textbook of Medicine, edited by Bennet, J.C. and Plum F., 20th edition, vol. 1, 1996, 1004-1010.
Cohen, P., "The development and therapeutic potential of protein kinase inhibitors", Current Opinion in Chemical Biology, vol. 3, pp. 459-465 (1999).
Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).
Dermer, G.B., "Another Anniversary for the War on Cancer", Biotechnology, vol. 12, p. 320 (1994).
Di Stefano et al., "Detection, Characterization, and Inhibition of FGFR-TACC Fusions in IDH Wild-Type Glioma," Clinical Cancer Research, Jan. 21, 2015, vol. 21, No. 14, pp. 3307-3317.
Dieci, M.V., et al., Fibroblast Growth Factor Receptor Inhibitors as a Cancer Treatment: From a Biologic Rationale to Medical Perspectives, Cancer Discovery, vol. 3, No. 3, pp. 264-279 (Feb. 2013).
Dienstmann et al., "Genomic Aberrations in the FGFR Pathway: Opportunities for Targeted Therapies in Solid Tumors," Annals of Oncology, vol. 25, Nov. 20, 2013, No. 3, pp. 552-563.
Dorwald, F.Z., Side Reactions in Organic Synthesis: A Guide to Successful Synthesis Design, Weinheim: WILEY-VCH Verlag GmbH & Co. KGaA, 2005, ISBN: 3-527-31021.5.
Freshney et al., Culture of Animal Cells, A Manual of Basic Technique, Alan R. Liss, Inc., 1983, New York, p. 4.
Fujita, M., et al., Generation of Formaldehyde by Pharmaceutical Excipients and Its Absorption by Meglumine, Chem. Pharm. Bull, vol. 57, No. 10, pp. 1096-1099 (2009).
Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).
Garuti, L., et al., Irreversible Protein Kinase Inhibitors, Current Medicinal Chemistry, vol. 18, No. 20, Jul. 1, 2011, pp. 2981-2994.
Golub, T.R., et al., "Molecular Classification of Cancer: Class Discovery and Class Prediction by Gene Expression Monitoring", Science, vol. 286, pp. 531-537 (1999).
Greulich, H., et al., "Targeting mutant fibroblast growth factor receptors in cancer", Trends in Molecular Medicine, vol. 17, No. 5, pp. 283-292 (2011).
Hackam, D.G., et al., Translation of Research Evidence From Animals to Humans, JAMA, vol. 14, pp. 1731-1732 (2006).
Ho, H.K., et al., "Current strategies for inhibiting FGFR activities in clinical applications: opportunities, challenges and toxicological considerations", Drug Discovery Today, vol. 19, Issue 1, pp. 51-62 (2014).
Hynes, N.E., et al., "Potential for Targeting the Fibroblast Growth Factor Receptors in Breast Cancer", Cancer Research, vol. 70, pp. 5199-5202 (2010).
International Search Report for PCT/EP2015/056507 dated Jul. 2, 2015.
Jain, V.K., et al., "Challenges and opportunities in the targeting of fibroblast growth factor receptors in breast cancer", Breast Cancer Research, vol. 14, No. 208, pp. 1-9 (2012).
Jordan, V.C., Tamoxifen: A Most Unlikely Pioneering Medicine, Nature Reviews: Drug Discovery, vol. 2, pp. 205-213 (2003).
Katoh et al., "FGFR inhibitors: Effects on Cancer Cells, Tumor Microenvironment and Whole-Body Homeostasis (Review)," International Journal of Molecular Medicine 2016, 38(1), pp. 3-15.
Katoh et al., International Journal of Molecular Medicine 23, 2009, 307-311.
Liang et al. Cytokine & Growth Factor Reviews 24, 2013, 467-475.
Lima, L.M., et al., "Bioisosterism: A Useful Strategy for Molecular Modification and Drug Design", Current Medical Chemistry, vol. 12(1), pp. 23-49 (2005).

(56) References Cited

OTHER PUBLICATIONS

Matsuda, Y., et al., Fibroblast Growth Factor Receptor-2 IIIc as a Novel Molecular Target in Colorectal Cancer, Current Colorectal Cancer Reports, vol. 10, No. 1, pp. 20-26 (2014).
Neidle, Stephen, ed. Cancer Drug Design and Discovery, (Elsevier/Academic Press), pp. 427-431, 2008.
Orre, Maxine and Rogers, Peter A.W. "VEGF, VEGFR-1, VEGFR-2, Microvessel Density and Endothelial Cell Proliferation in Tumours of the Ovary", Int. J. Cancer (Pred. Oncol), vol. 84(2), 1999, pp. 101-108.
Parker et al., "Emergence of FGFR Family Gene Fusions as Therapeutic Targets in a Wide Spectrum of Solid Tumours," Journal of Pathology, Oct. 29, 2013, vol. 232, No. 1, pp. 4-15.
Patani, G.A., et al., "Bioisosterism: A Rational Approach in Drug Design", Chem. Rev. vol. 96, pp. 3147-3176 (1996).
Rodriguez-Vida, A., et al., "Complexity of FGFR signaling in metastatic urothelial cancer", Journal of Hematology & Oncology, vol. 8, pp. 119 et seq. (2015).
Sonpavde, G., et al., "Fibroblast growth factor receptors as therapeutic targets in clear-cell renal cell carcinoma", Expert Opinion on Investigational Drugs, vol. 23, Issue 3, pp. 305-315 (2014).
Study to Assess the Relative Bioavailability of Orally Administered JNJ-42756493 Tablet Versus JNJ42756493 Capsule in Healthy Participants, ClinicalTrials.gov, pp. 1-4 (2014).
Thompson, Andrew M. et al. "Synthesis and Structure—Activity Relationships of 7-Substituted 3-(2,6-Dich1 oropheny 1)-1.6-naptilyridi n-2(1 //)—oncs as Selective Inhibitors of pp60c-JTC", Journal of Medicinal Chemistry, vol. 43, No. 16, 2000, pp. 3134-3147.
V. Hikkinvottom, "Reakcii Organicheskih Soedinenij" Gosudarstvennoe ob#teninennoe nauchno-technicheskoe izdatefstvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
Vippagunta, S.R. et al., Crystalline Solids, Advanced Drug Delivery Reviews, vol. 48, pp. 3-26 (2001).
Yan, Lin et al. "An efficient synthesis of quinoxaline derivatives from 4-chloro-4-deoxy-a-D-galactose and their cytotoxic activities", Bioorganic & Medicinal Chemistry Letters, vol. 17, No. 3, 2006, pp. 609-612.
Zhou, Wenjun et al., "A Structure-Guided Approach to Creating Covalent FGFR Inhibitors", Chemistry & Biology, vol. 17, pp. 285-295 (2010).

\* cited by examiner

BI-HETEROARYL SUBSTITUTE 1,4-BENZODIAZEPINES AND USES THEREOF FOR THE TREATMENT OF CANCER

This application is a national stage of PCT Application No. PCT/US2016/072501, filed Sep. 22, 2016, which claims priority to EPO Patent Application No. 15186478.2, filed Sep. 23, 2015. The entire disclosures of each of these patent applications are hereby incorporated in their entirety.

FIELD OF THE INVENTION

The invention relates to new quinoline, pyridopyrazine, naphthyridine and quinazolinone derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I):

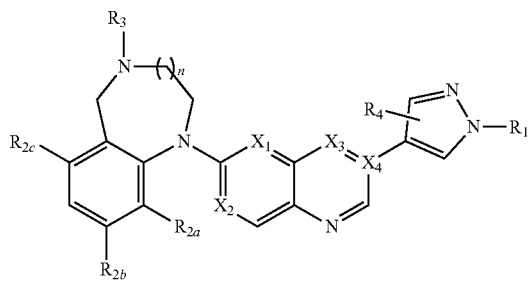

(I)

including any tautomeric or stereochemically isomeric form thereof, wherein $X_1$ is CH, $X_2$ is CH; $X_3$ is CH and $X_4$ is C (a);

$X_1$ is N, $X_2$ is CH, $X_3$ is N and $X_4$ is C (b);

$X_1$ is N, $X_2$ is CH, $X_3$ is CH and $X_4$ is C (c); or $X_1$ is CH, $X_2$ is CH, $X_3$ is C(=O) and $X_4$ is N (d);

and wherein the doted line represents a bond in case of (a), (b) and (c) and wherein the dotted line is absent in case of (d);

n represents an integer equal to 1 or 2;

$R_1$ represents hydrogen, $C_{1-6}$alkyl, hydroxy$C_{1-6}$alkyl, $C_{1-6}$alkyl substituted with —C(=O)NHCH$_3$, or $C_{1-6}$alkyl substituted with —S(=O)$_2$—$C_{1-4}$ alkyl;

$R_{2a}$ represents hydrogen, fluoro or chloro;

$R_{2b}$ represents methoxy or hydroxyl;

$R_{2c}$ represents methoxy or hydroxyl;

$R_3$ represent hydrogen, $C_{1-6}$alkyl, $C_{3-6}$cycloalkyl, or $C_{1-2}$alkyl substituted with $C_{3-6}$cycloalkyl;

$R_4$ represents hydrogen, methyl or ethyl;

the pharmaceutically acceptable salts thereof or the solvates thereof.

In one embodiment there is provided compounds of formula (Ia):

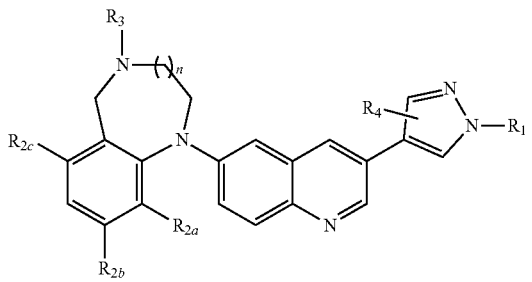

(Ia)

including any tautomeric or stereochemically isomeric form thereof, wherein n represents an integer equal to 1 or 2;

$R_1$ represents hydrogen, $C_{1-6}$alkyl, hydroxy$C_{1-6}$alkyl, $C_{1-6}$alkyl substituted with —C(=O)NHCH$_3$, or $C_{1-6}$alkyl substituted with —S(=O)$_2$—$C_{1-4}$ alkyl;

$R_{2a}$ represents hydrogen, fluoro or chloro;

$R_{2b}$ represents methoxy or hydroxyl;

$R_{2c}$ represents methoxy or hydroxyl;

$R_3$ represent hydrogen, $C_{1-6}$alkyl, $C_{3-6}$cycloalkyl, or $C_{1-2}$alkyl substituted with $C_{3-6}$cycloalkyl;

$R_4$ represents hydrogen, methyl or ethyl;

the pharmaceutically acceptable salts thereof or the solvates thereof.

In one embodiment there is provided compounds of formula (Ib):

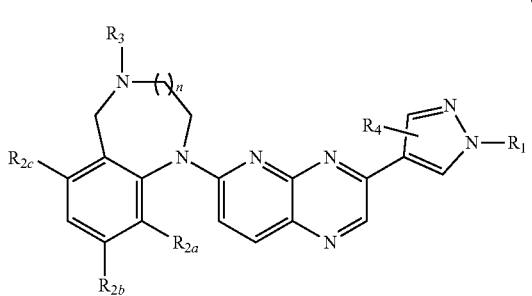

(Ib)

including any tautomeric or stereochemically isomeric form thereof, wherein n represents an integer equal to 1 or 2;

$R_1$ represents hydrogen, $C_{1-6}$alkyl, hydroxy$C_{1-6}$alkyl, $C_{1-6}$alkyl substituted with —C(=O)NHCH$_3$, or $C_{1-6}$alkyl substituted with —S(=O)$_2$—$C_{1-4}$ alkyl;

$R_{2a}$ represents hydrogen, fluoro or chloro;

$R_{2b}$ represents methoxy or hydroxyl;

$R_{2c}$ represents methoxy or hydroxyl;

$R_3$ represent hydrogen, $C_{1-6}$alkyl, $C_{3-6}$cycloalkyl, or $C_{1-2}$alkyl substituted with $C_{3-6}$cycloalkyl;

$R_4$ represents hydrogen, methyl or ethyl;

the pharmaceutically acceptable salts thereof or the solvates thereof.

In one embodiment there is provided compounds of formula (Ic):

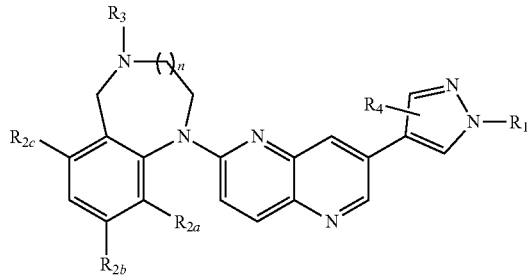

including any tautomeric or stereochemically isomeric form thereof, wherein
n represents an integer equal to 1 or 2;
$R_1$ represents hydrogen, $C_{1-6}$alkyl, hydroxy$C_{1-6}$alkyl, $C_{1-6}$alkyl substituted with —C(=O)NHCH$_3$, or $C_{1-6}$alkyl substituted with —S(=O)$_2$—$C_{1-4}$ alkyl;
$R_{2a}$ represents hydrogen, fluoro or chloro;
$R_{2b}$ represents methoxy or hydroxyl; $R_{2c}$ represents methoxy or hydroxyl;
$R_3$ represent hydrogen, $C_{1-6}$alkyl, $C_{3-6}$cycloalkyl, or $C_{1-2}$alkyl substituted with $C_{3-6}$cycloalkyl;
$R_4$ represents hydrogen, methyl or ethyl;
the pharmaceutically acceptable salts thereof or the solvates thereof.

In one embodiment there is provided compounds of formula (Id):

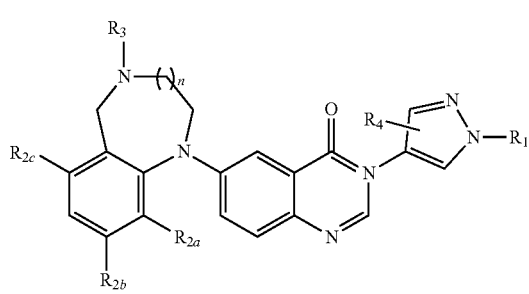

including any tautomeric or stereochemically isomeric form thereof, wherein
n represents an integer equal to 1 or 2;
$R_1$ represents hydrogen, $C_{1-6}$alkyl, hydroxy$C_{1-6}$alkyl, $C_{1-6}$alkyl substituted with —C(=O)NHCH$_3$, or $C_{1-6}$alkyl substituted with —S(=O)$_2$—$C_{1-4}$ alkyl;
$R_{2a}$ represents hydrogen, fluoro or chloro;
$R_{2b}$ represents methoxy or hydroxyl;
$R_{2c}$ represents methoxy or hydroxyl;
$R_3$ represent hydrogen, $C_{1-6}$alkyl, $C_{3-6}$cycloalkyl, or $C_{1-2}$alkyl substituted with $C_{3-6}$cycloalkyl;
$R_4$ represents hydrogen, methyl or ethyl;
the pharmaceutically acceptable salts thereof or the solvates thereof.

WO2006/092430, WO2008/003702, WO01/68047, WO2005/007099, WO2004/098494, WO2009/141386, WO2004/030635, WO2008/141065, WO2011/026579, WO2011/028947, WO2007/003419, WO00/42026, WO2012/154760, WO2011/047129, WO2003/076416, WO2002/096873, WO2000/055153, EP548934, U.S. Pat. No. 4,166,117, WO2011/135376, WO2012/073017, WO2013/061074, WO2013/061081, WO2013/061077, WO2013/061080, WO2013/179034, WO2013/179033, WO2014/174307, WO2015/144803, WO2015/144804, WO2015/144808 which each disclose a series of heterocyclyl derivatives.

DETAILED DESCRIPTION OF THE INVENTION

Unless the context indicates otherwise, references to formula (I) in all sections of this document (including the uses, methods and other aspects of the invention) include references to all other sub-formula (e.g. Ia, Ib, Ic, Id), sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a hydroxy$C_{1-6}$alkyl group contains from 1 to 6 carbon atoms, and so on.

The term '$C_{1-2}$alkyl', '$C_{1-4}$alkyl', or '$C_{1-6}$alkyl' as used herein as a group or part of a group refers to a linear or branched saturated hydrocarbon group containing 1 or 2, or from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl, cyclohexyl.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

Whenever used hereinbefore or hereinafter that substituents can be selected each independently out of a list of numerous definitions, all possible combinations are intended which are chemically possible.

In one embodiment, in a compound of formula (I), (Ia), (Ib), (Ic) or (Id), n represents an integer equal to 1.

In one embodiment, in a compound of formula (I), (Ia), (Ib), (Ic) or (Id), n represents an integer equal to 2.

In one embodiment, in a compound of formula (I), (Ia), (Ib), (Ic) or (Id), $R_1$ represents hydrogen or $C_{1-6}$alkyl, in particular $C_{1-6}$alkyl, more in particular methyl.

In one embodiment, in a compound of formula (I), (Ia), (Ib), (Ic) or (Id), $R_1$ represents hydrogen.

In one embodiment, in a compound of formula (I), (Ia), (Ib), (Ic) or (Id), $R_{2a}$ represents hydrogen or fluoro.

In one embodiment, in a compound of formula (I), (Ia), (Ib), (Ic) or (Id), $R_{2a}$ represents hydrogen.

In one embodiment, in a compound of formula (I), (Ia), (Ib), (Ic) or (Id), $R_{2a}$ represents fluoro.

In one embodiment, in a compound of formula (I), (Ia), (Ib), (Ic) or (Id), $R_{2a}$ represents fluoro or chloro, in particular fluoro.

In one embodiment, in a compound of formula (I), (Ia), (Ib), (Ic) or (Id), $R_{2b}$ represents methoxy.

In one embodiment, in a compound of formula (I), (Ia), (Ib), (Ic) or (Id), $R_{2b}$ represents hydroxy.

In one embodiment, in a compound of formula (I), (Ia), (Ib), (Ic) or (Id), $R_{2c}$ represents methoxy.

In one embodiment, in a compound of formula (I), (Ia), (Ib), (Ic) or (Id), $R_{2c}$ represents hydroxy.

In one embodiment, in a compound of formula (I), (Ia), (Ib), (Ic) or (Id), $R_{2b}$ represents methoxy and $R_{2c}$ represents hydroxyl.

In one embodiment, in a compound of formula (I), (Ia), (Ib), (Ic) or (Id), $R_{2b}$ represents hydroxyl and $R_{2c}$ represents methoxy.

In one embodiment, in a compound of formula (I), (Ia), (Ib), (Ic) or (Id), $R_{2b}$ and $R_{2c}$ both represent methoxy.

In one embodiment, in a compound of formula (I), (Ia), (Ib), (Ic) or (Id), $R_{2b}$ and $R_{2c}$ both represent hydroxyl.

In one embodiment, in a compound of formula (I), (Ia), (Ib), (Ic) or (Id), $R_3$ represents hydrogen.

In one embodiment, in a compound of formula (I), (Ia), (Ib), (Ic) or (Id), $R_3$ represents $C_{1-6}$alkyl, in particular $C_{1-4}$alkyl, even more in particular methyl or isopropyl, in particular isopropyl.

In one embodiment, in a compound of formula (I), (Ia), (Ib), (Ic) or (Id), $R_4$ represents hydrogen.

In one embodiment, in a compound of formula (I), one or more of the following, in particular all of the following, apply:
n represents an integer equal to 1;
$R_1$ represents hydrogen or $C_{1-6}$alkyl, in particular $C_{1-6}$alkyl, more in particular $C_{1-4}$alkyl, even more in particular methyl;
$R_{2a}$ represents hydrogen or fluoro;
$R_{2b}$ represents methoxy or hydroxyl, in particular methoxy;
$R_{2c}$ represents methoxy or hydroxyl, in particular methoxy;
$R_3$ represents $C_{1-6}$alkyl, in particular $C_{1-4}$alkyl, even more in particular methyl or isopropyl, in particular isopropyl;
$R_4$ represents hydrogen.

In one embodiment, in a compound of formula (I), n represents an integer equal to 2.

In one embodiment, in a compound of formula (I), n represents an integer equal to 1.

In one embodiment, in a compound of formula (I), $R_1$ represents hydrogen.

In one embodiment, in a compound of formula (I), $R_1$ represents $C_{1-6}$alkyl, in particular $C_{1-4}$alkyl, even more in particular methyl.

In one embodiment, in a compound of formula (I), $R_{2a}$ represents hydrogen.

In one embodiment, in a compound of formula (I), $R_{2a}$ represents fluoro or chloro, in particular fluoro.

In one embodiment, in a compound of formula (I), $R_{2b}$ represents methoxy.

In one embodiment, in a compound of formula (I), $R_{2b}$ represents hydroxy.

In one embodiment, in a compound of formula (I), $R_{2c}$ represents methoxy.

In one embodiment, in a compound of formula (I), $R_{2c}$ represents hydroxy.

In one embodiment, in a compound of formula (I), $R_{2b}$ represents methoxy and $R_{2c}$ represents hydroxyl.

In one embodiment, in a compound of formula (I), $R_{2b}$ represents hydroxyl and $R_{2c}$ represents methoxy.

In one embodiment, in a compound of formula (I), $R_{2b}$ and $R_{2c}$ both represent methoxy.

In one embodiment, in a compound of formula (I), $R_{2b}$ and $R_{2c}$ both represent hydroxyl.

In one embodiment, in a compound of formula (I), $R_3$ represents hydrogen.

In one embodiment, in a compound of formula (I), $R_3$ represents $C_{1-6}$alkyl, in particular $C_{1-4}$alkyl, even more in particular methyl or isopropyl, in particular isopropyl.

In one embodiment, in a compound of formula (I), $R_4$ represents hydrogen.

In one embodiment, in a compound of formula (Ia), one or more of the following, in particular all of the following, apply:
n represents an integer equal to 1;
$R_1$ represents hydrogen or $C_{1-6}$alkyl, in particular $C_{1-6}$alkyl, more in particular $C_{1-4}$alkyl, even more in particular methyl;
$R_{2a}$ represents hydrogen or fluoro, in particular hydrogen;
$R_{2b}$ represents methoxy or hydroxyl, in particular methoxy;
$R_{2c}$ represents methoxy or hydroxyl, in particular methoxy;
$R_3$ represents $C_{1-6}$alkyl, in particular $C_{1-4}$alkyl, even more in particular methyl or isopropyl, in particular isopropyl;
$R_4$ represents hydrogen.

In one embodiment, in a compound of formula (Ia), n represents an integer equal to 2.

In one embodiment, in a compound of formula (Ia), n represents an integer equal to 1.

In one embodiment, in a compound of formula (Ia), $R_1$ represents hydrogen.

In one embodiment, in a compound of formula (Ia), $R_1$ represents $C_{1-6}$alkyl, in particular $C_{1-4}$alkyl, even more in particular methyl.

In one embodiment, in a compound of formula (Ia), $R_{2a}$ represents hydrogen.

In one embodiment, in a compound of formula (Ia), $R_{2a}$ represents fluoro or chloro, in particular fluoro.

In one embodiment, in a compound of formula (Ia), $R_{2b}$ represents methoxy.

In one embodiment, in a compound of formula (Ia), $R_{2b}$ represents hydroxy.

In one embodiment, in a compound of formula (Ia), $R_{2c}$ represents methoxy.

In one embodiment, in a compound of formula (Ia), $R_{2c}$ represents hydroxy.

In one embodiment, in a compound of formula (Ia), $R_{2b}$ represents methoxy and $R_{2c}$ represents hydroxyl.

In one embodiment, in a compound of formula (Ia), $R_{2b}$ represents hydroxyl and $R_{2c}$ represents methoxy.

In one embodiment, in a compound of formula (Ia), $R_{2b}$ and $R_{2c}$ both represent methoxy.

In one embodiment, in a compound of formula (Ia), $R_{2b}$ and $R_{2c}$ both represent hydroxyl.

In one embodiment, in a compound of formula (Ia), $R_3$ represents hydrogen.

In one embodiment, in a compound of formula (Ia), $R_3$ represents $C_{1-6}$alkyl, in particular $C_{1-4}$alkyl, even more in particular methyl or isopropyl, in particular isopropyl.

In one embodiment, in a compound of formula (Ia), $R_4$ represents hydrogen.

In one embodiment, in a compound of formula (Ib), one or more of the following, in particular all of the following, apply:
n represents an integer equal to 1;
$R_1$ represents hydrogen or $C_{1-6}$alkyl, in particular $C_{1-6}$alkyl, more in particular $C_{1-4}$alkyl, even more in particular methyl;
$R_{2a}$ represents hydrogen or fluoro;
$R_{2b}$ represents methoxy or hydroxyl, in particular methoxy;

$R_{2c}$ represents methoxy or hydroxyl, in particular methoxy;
$R_3$ represents $C_{1-6}$alkyl, in particular $C_{1-4}$alkyl, even more in particular methyl or isopropyl, in particular isopropyl;
$R_4$ represents hydrogen.

In one embodiment, in a compound of formula (Ib), n represents an integer equal to 2.

In one embodiment, in a compound of formula (Ib), n represents an integer equal to 1.

In one embodiment, in a compound of formula (Ib), $R_1$ represents hydrogen.

In one embodiment, in a compound of formula (Ib), $R_1$ represents $C_{1-6}$alkyl, in particular $C_{1-4}$alkyl, even more in particular methyl.

In one embodiment, in a compound of formula (Ib), $R_{2a}$ represents hydrogen.

In one embodiment, in a compound of formula (Ib), $R_{2a}$ represents fluoro or chloro, in particular fluoro.

In one embodiment, in a compound of formula (Ib), $R_{2b}$ represents methoxy.

In one embodiment, in a compound of formula (Ib), $R_{2b}$ represents hydroxy.

In one embodiment, in a compound of formula (Ib), $R_{2c}$ represents methoxy.

In one embodiment, in a compound of formula (Ib), $R_{2c}$ represents hydroxy.

In one embodiment, in a compound of formula (Ib), $R_{2b}$ represents methoxy and $R_{2c}$ represents hydroxyl.

In one embodiment, in a compound of formula (Ib), $R_{2b}$ represents hydroxyl and $R_{2c}$ represents methoxy.

In one embodiment, in a compound of formula (Ib), $R_{2b}$ and $R_{2c}$ both represent methoxy.

In one embodiment, in a compound of formula (Ib), $R_{2b}$ and $R_{2c}$ both represent hydroxyl.

In one embodiment, in a compound of formula (Ib), $R_3$ represents hydrogen.

In one embodiment, in a compound of formula (Ib), $R_3$ represents $C_{1-6}$alkyl, in particular $C_{1-4}$alkyl, even more in particular methyl or isopropyl, in particular isopropyl.

In one embodiment, in a compound of formula (Ib), $R_4$ represents hydrogen.

In one embodiment, in a compound of formula (Ic), one or more of the following, in particular all of the following, apply:
n represents an integer equal to 1;
$R_1$ represents hydrogen or $C_{1-6}$alkyl, in particular $C_{1-6}$alkyl, more in particular $C_{1-4}$alkyl, even more in particular methyl;
$R_{2a}$ represents hydrogen or fluoro;
$R_{2b}$ represents methoxy or hydroxyl, in particular methoxy;
$R_{2c}$ represents methoxy or hydroxyl, in particular methoxy;
$R_3$ represents $C_{1-6}$alkyl, in particular $C_{1-4}$alkyl, even more in particular methyl or isopropyl, in particular isopropyl;
$R_4$ represents hydrogen.

In one embodiment, in a compound of formula (Ic), n represents an integer equal to 2.

In one embodiment, in a compound of formula (Ic), n represents an integer equal to 1.

In one embodiment, in a compound of formula (Ic), $R_1$ represents hydrogen.

In one embodiment, in a compound of formula (Ic), $R_1$ represents $C_{1-6}$alkyl, in particular $C_{1-4}$alkyl, even more in particular methyl.

In one embodiment, in a compound of formula (Ic), $R_{2a}$ represents hydrogen.

In one embodiment, in a compound of formula (Ic), $R_{2a}$ represents fluoro or chloro, in particular fluoro.

In one embodiment, in a compound of formula (Ic), $R_{2b}$ represents methoxy.

In one embodiment, in a compound of formula (Ic), $R_{2b}$ represents hydroxy.

In one embodiment, in a compound of formula (Ic), $R_{2c}$ represents methoxy.

In one embodiment, in a compound of formula (Ic), $R_{2c}$ represents hydroxy.

In one embodiment, in a compound of formula (Ic), $R_{2b}$ represents methoxy and $R_{2c}$ represents hydroxyl.

In one embodiment, in a compound of formula (Ic), $R_{2b}$ represents hydroxyl and $R_{2c}$ represents methoxy.

In one embodiment, in a compound of formula (Ic), $R_{2b}$ and $R_{2c}$ both represent methoxy.

In one embodiment, in a compound of formula (Ic), $R_{2b}$ and $R_{2c}$ both represent hydroxyl.

In one embodiment, in a compound of formula (Ic), $R_3$ represents hydrogen.

In one embodiment, in a compound of formula (Ic), $R_3$ represents $C_{1-6}$alkyl, in particular $C_{1-4}$alkyl, even more in particular methyl or isopropyl, in particular isopropyl.

In one embodiment, in a compound of formula (Ic), $R_4$ represents hydrogen.

In one embodiment, in a compound of formula (Id), one or more of the following, in particular all of the following, apply:
n represents an integer equal to 1;
$R_1$ represents hydrogen or $C_{1-6}$alkyl, in particular $C_{1-6}$alkyl, more in particular $C_{1-4}$alkyl, even more in particular methyl;
$R_{2a}$ represents hydrogen or fluoro;
$R_{2b}$ represents methoxy or hydroxyl, in particular methoxy;
$R_{2c}$ represents methoxy or hydroxyl, in particular methoxy;
$R_3$ represents $C_{1-6}$alkyl, in particular $C_{1-4}$alkyl, even more in particular methyl or isopropyl, in particular isopropyl;
$R_4$ represents hydrogen.

In one embodiment, in a compound of formula (Id), n represents an integer equal to 2.

In one embodiment, in a compound of formula (Id), n represents an integer equal to 1.

In one embodiment, in a compound of formula (Id), $R_1$ represents hydrogen.

In one embodiment, in a compound of formula (Id), $R_1$ represents $C_{1-6}$alkyl, in particular $C_{1-4}$alkyl, even more in particular methyl.

In one embodiment, in a compound of formula (Id), $R_{2a}$ represents hydrogen.

In one embodiment, in a compound of formula (Id), $R_{2a}$ represents fluoro or chloro, in particular fluoro.

In one embodiment, in a compound of formula (Id), $R_{2b}$ represents methoxy.

In one embodiment, in a compound of formula (Id), $R_{2b}$ represents hydroxy.

In one embodiment, in a compound of formula (Id), $R_{2c}$ represents methoxy.

In one embodiment, in a compound of formula (Id), $R_{2c}$ represents hydroxy.

In one embodiment, in a compound of formula (Id), $R_{2b}$ represents methoxy and $R_{2c}$ represents hydroxyl.

In one embodiment, in a compound of formula (Id), $R_{2b}$ represents hydroxyl and $R_{2c}$ represents methoxy.

In one embodiment, in a compound of formula (Id), $R_{2b}$ and $R_{2c}$ both represent methoxy.

In one embodiment, in a compound of formula (Id), $R_{2b}$ and $R_{2c}$ both represent hydroxyl.

In one embodiment, in a compound of formula (Id), $R_3$ represents hydrogen.

In one embodiment, in a compound of formula (Id), $R_3$ represents $C_{1-6}$alkyl, in particular $C_{1-4}$alkyl, even more in particular methyl or isopropyl, in particular isopropyl.

In one embodiment, in a compound of formula (Id), $R_4$ represents hydrogen.
In one embodiment, the compound of formula (I) as defined herein is selected from the following compounds or is one of the following compounds:
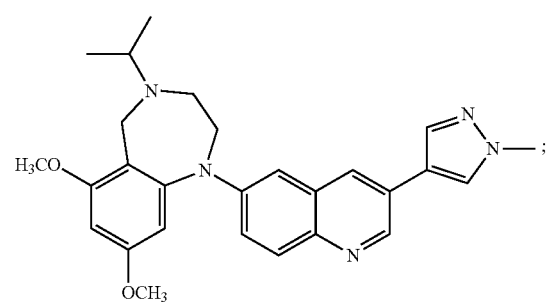
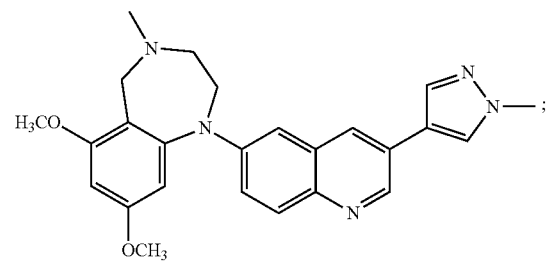
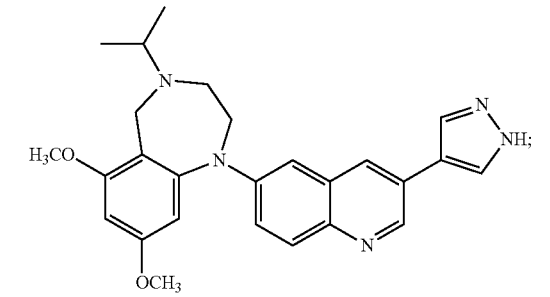
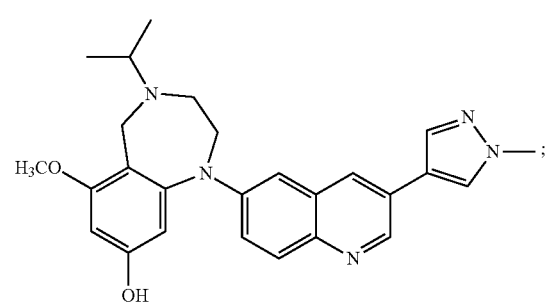
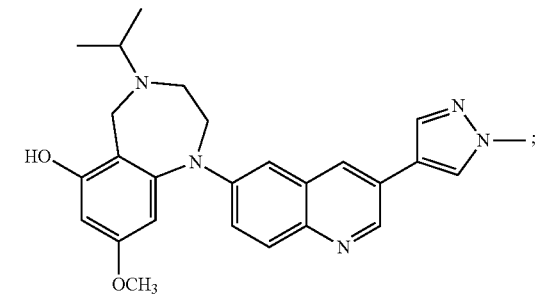
-continued
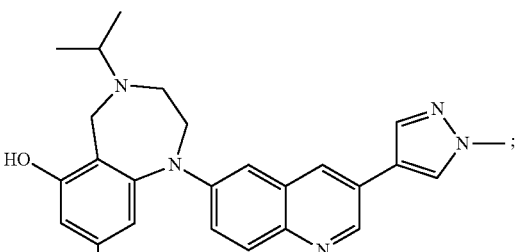
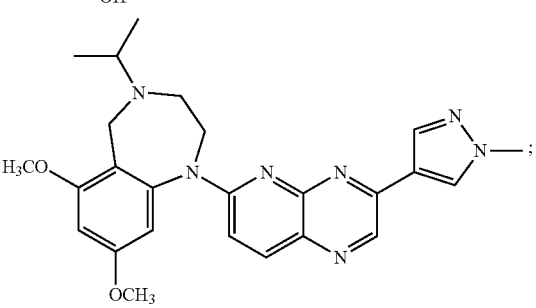
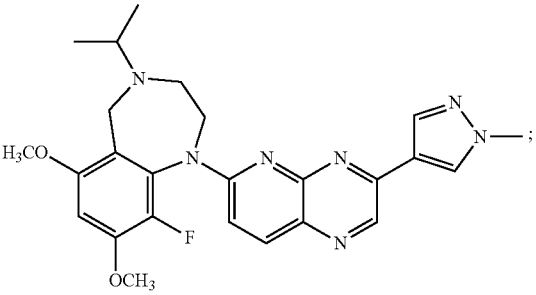
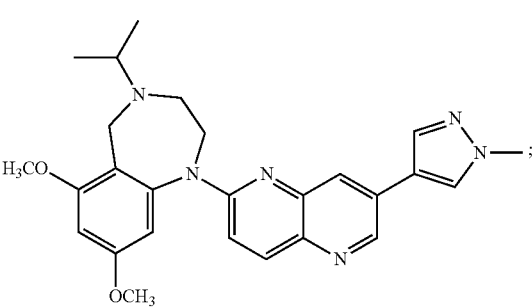
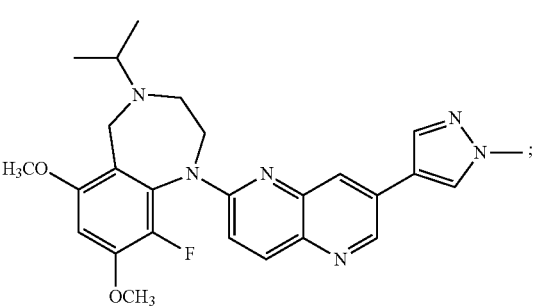

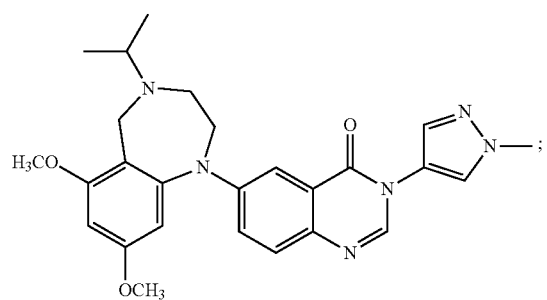
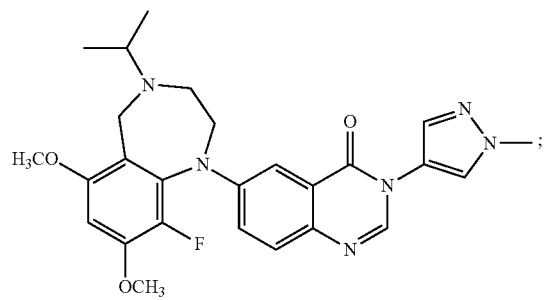
a pharmaceutically acceptable salt thereof or a solvate thereof.
In one embodiment, the compound of formula (I) as defined herein is selected from the following compounds or is one of the following compounds:
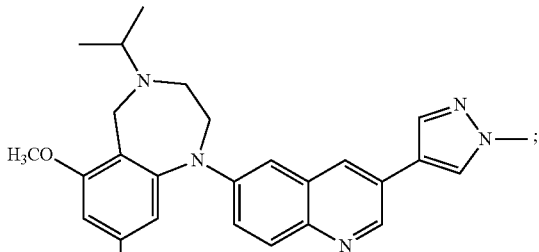
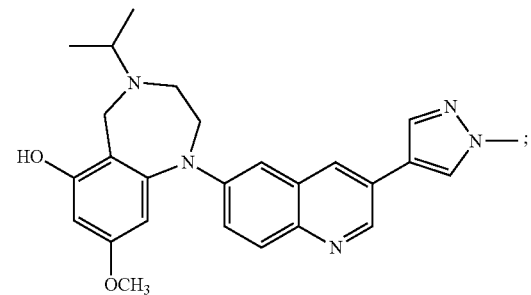
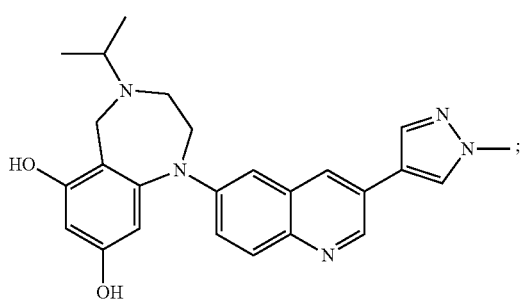 [SMILES: CC(C)N1CCN(c2ccc3ncc(-c4cnn(C)c4)cc3c2)c2cc(O)cc(O)c2C1]
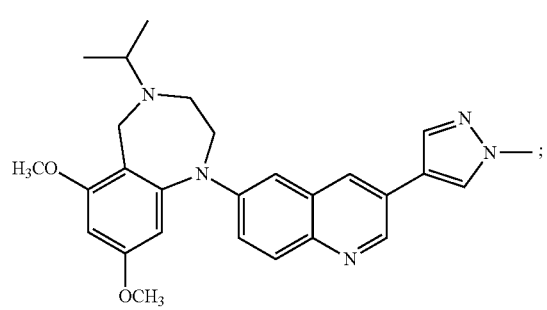
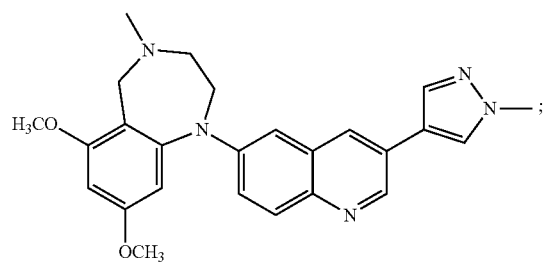
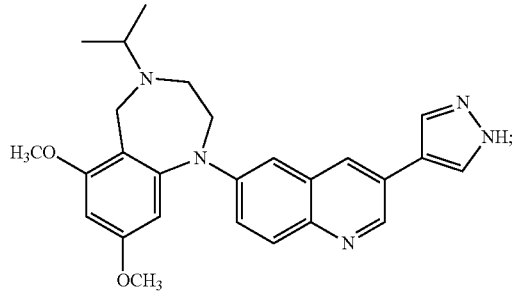
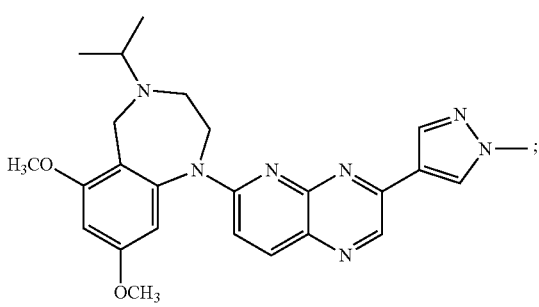
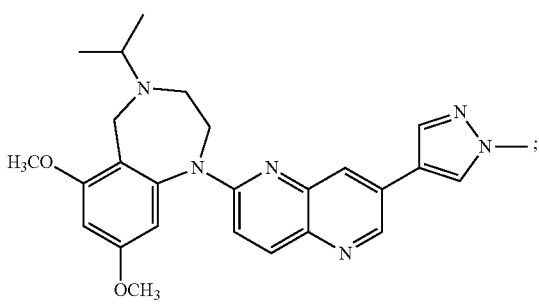

-continued
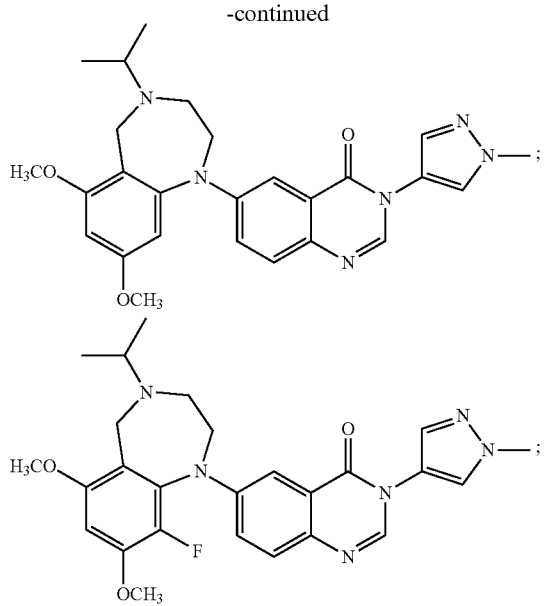
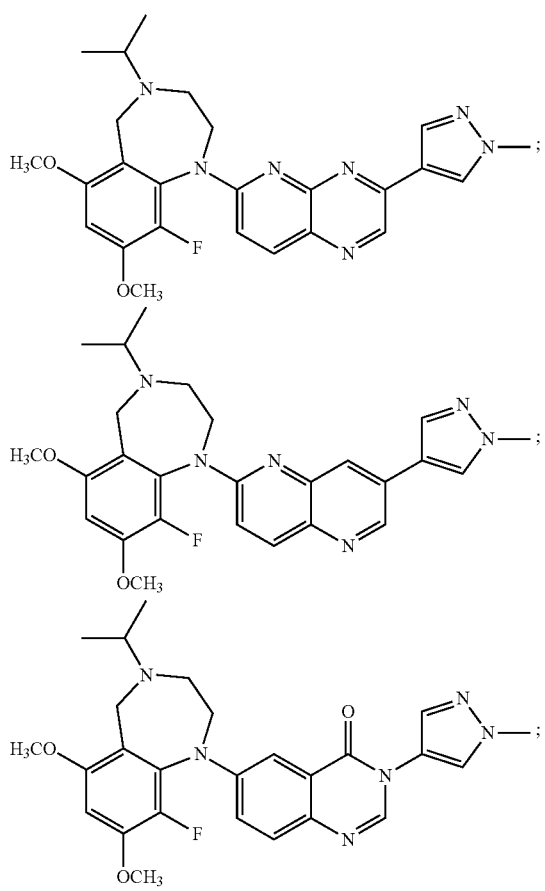
a pharmaceutically acceptable salt thereof or a solvate thereof.
In one embodiment, the compound of formula (I) as defined herein is selected from the following compounds or is one of the following compounds:
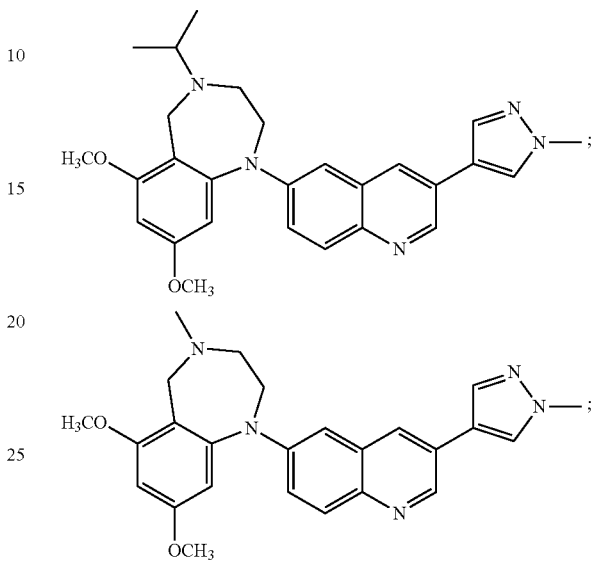
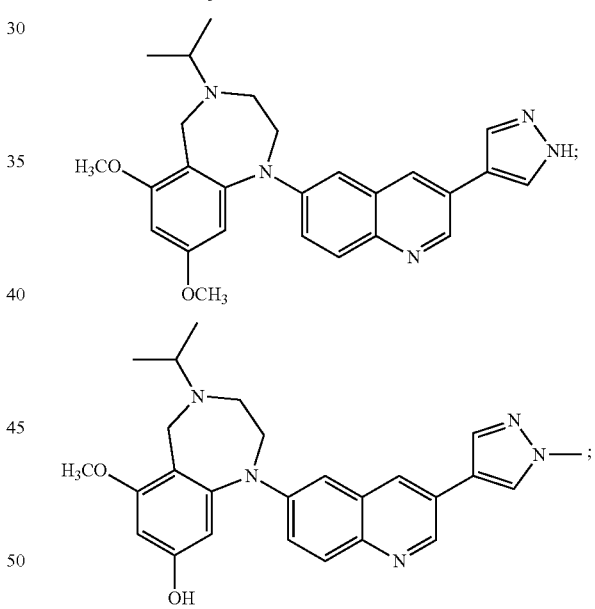
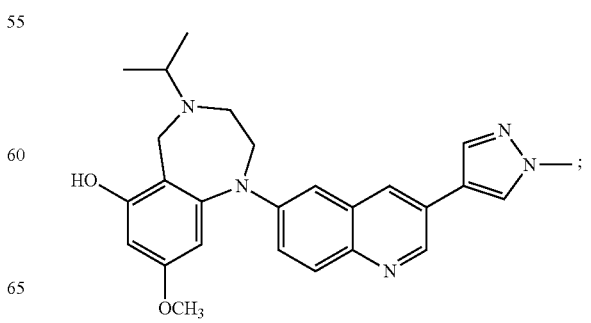

-continued

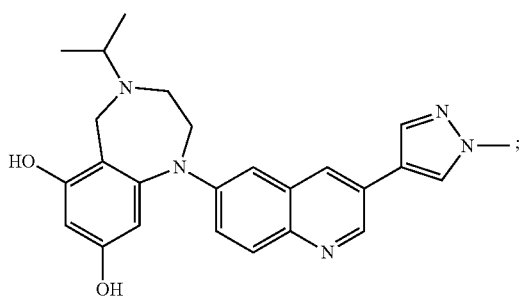

a pharmaceutically acceptable salt thereof or a solvate thereof.

In one embodiment, the compound of formula (I) as defined herein is selected from the following compounds or is one of the following compounds:

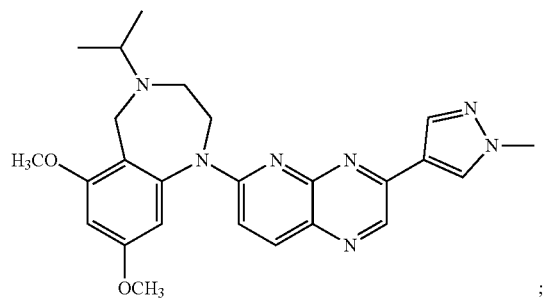

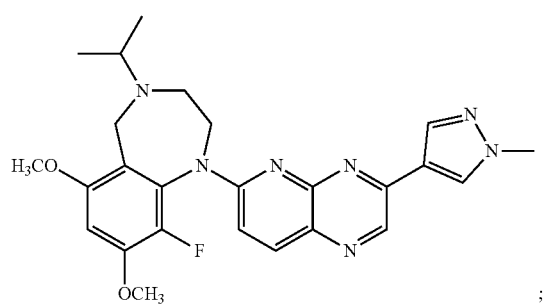

a pharmaceutically acceptable salt thereof or a solvate thereof.

In one embodiment, the compound of formula (I) as defined herein is selected from the following compounds or is one of the following compounds:

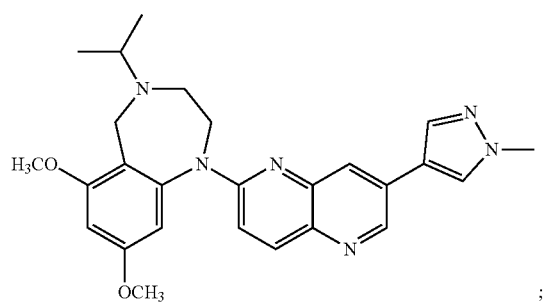

-continued

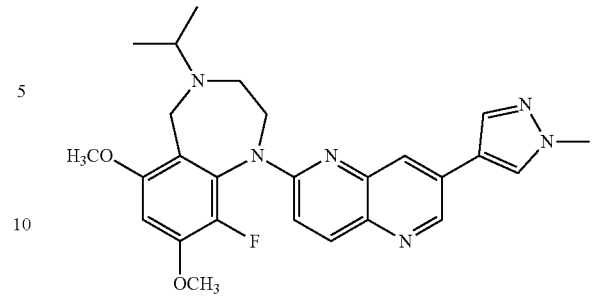

a pharmaceutically acceptable salt thereof or a solvate thereof.

In one embodiment, the compound of formula (I) as defined herein is selected from the following compounds or is one of the following compounds:

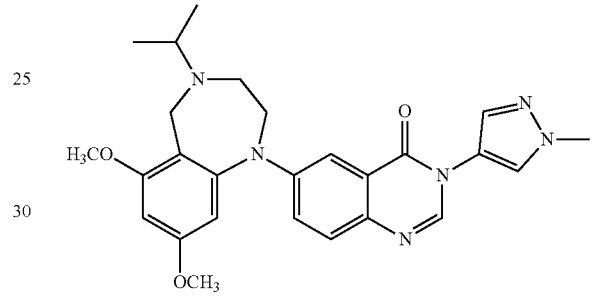

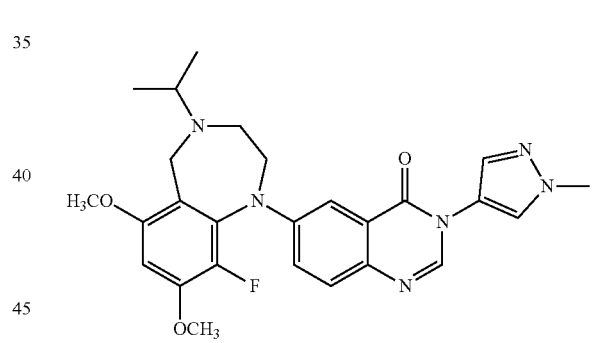

a pharmaceutically acceptable salt thereof or a solvate thereof.

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof as defined herein.

In general, compounds of formula (I) can be prepared according to the following reaction scheme 1.

Scheme 1

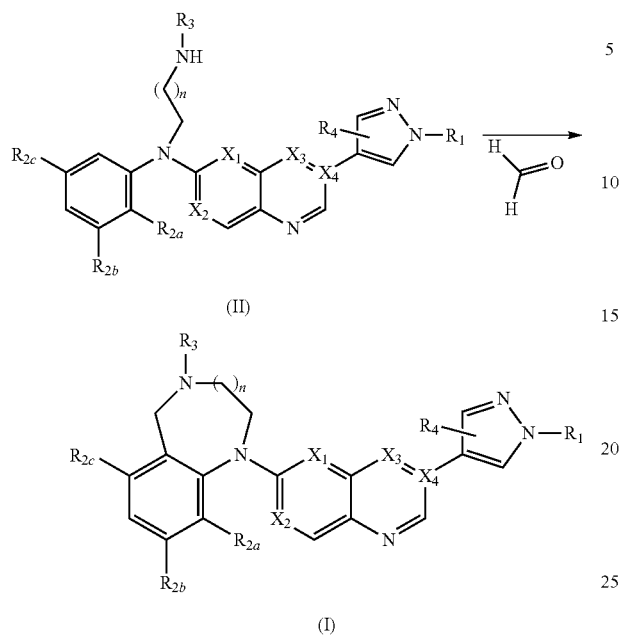

In Scheme 1, the following reaction conditions apply:

1: reaction of an intermediate of formula (II) with formaldehyde in the presence of a suitable solvent, such as for example dioxane, N,N-dimethylformamide, N,N-dimethylacetamide, at a temperature ranging from room temperature to reflux.

In general, compounds of formula (I) wherein $X_1$ is CH, $X_2$ is CH; $X_3$ is CH and $X_4$ is C (a);

$X_1$ is N, $X_2$ is CH, $X_3$ is N and $X_4$ is C (b); or $X_1$ is N, $X_2$ is CH, $X_3$ is CH and $X_4$ is C (c); and wherein the dotted line represents a bond, said compounds being represented by formula (Ie), can be prepared according to the following reaction Scheme 2. In Scheme 2, $W_1$ and $W_2$ represent suitable leaving groups, such as for example Cl, Br or I; $PG_1$ represents a suitable protective group, such as for example tert-butyl-dimethylsilyl; and $PG_2$ represents a suitable protective group, such as for example tert-butoxycarbonyl.

Scheme 2

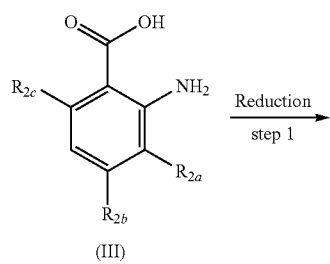

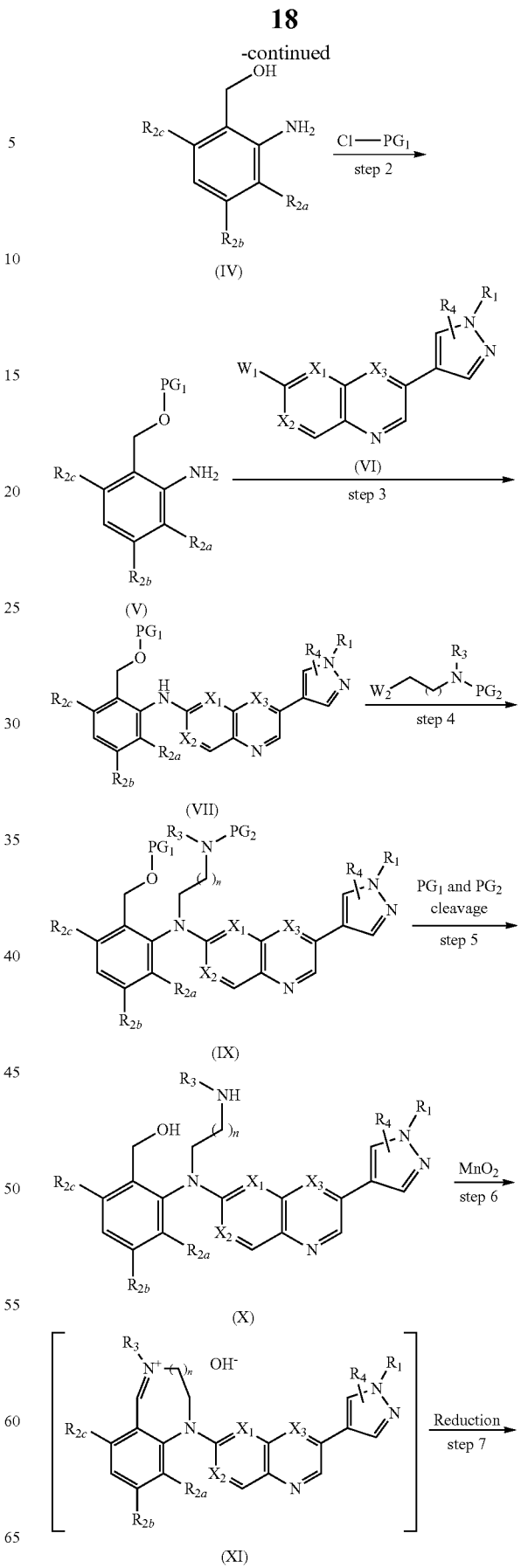

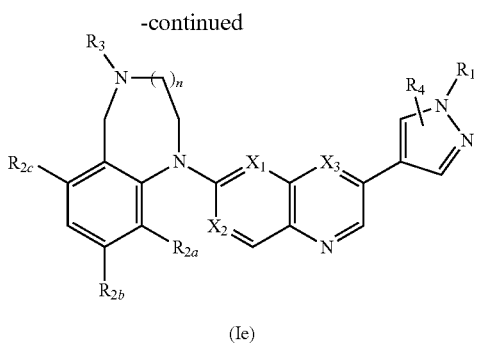

(Ie)

In Scheme 2, the following reaction conditions apply:
1: in the presence of a suitable reducing agent, such as for example lithium aluminium hydride, in a suitable solvent, such as for example diethylether, at a suitable temperature, such as for example in the range from 0° C. to room temperature;
2: in the presence of a suitable deprotonating agent, such as for example sodium hydride, in a suitable solvent, such as for example dimethylformamide;
3: for compounds wherein $X_1$ is CH, $X_2$ is CH; $X_3$ is CH and $X_4$ is C: in the presence of a suitable catalyst, such as for example a palladium catalyst, e.g. palladium acetate, a suitable ligand, such as for example rac-2,2'-bis-1,1'-binaphtyl, a suitable base, such as for example sodium tertbutoxide, a suitable solvent, such as for example dioxane, at a suitable temperature, such as for example 100° C.;
for compounds wherein $X_1$ is N, $X_2$ is CH, $X_3$ is N and $X_4$ is C: in the presence of a suitable solvent, such as for example an alcohol, e.g. 1-propanol, at a suitable temperature, such as for example 100° C.;
for compounds wherein $X_1$ is N, $X_2$ is CH, $X_3$ is CH and $X_4$ is C: in the presence of a suitable base, such as for example potassium bis(trimethylsilyl)amide, a suitable solvent, such as for example tetrahydrofuran, at a suitable temperature, such as for example in the range from 0° C. to room temperature;
4: in the presence of a suitable deprotonating agent, such as for example sodium hydride, and a suitable solvent such as for example dimethylformamide;
5: in the presence of a suitable acid, such as for example hydrochloric acid or trifluoroacetic acid, and a suitable solvent, such as for example an alcohol, e.g. methanol, or dichloromethane;
6: in the presence of a suitable solvent, such as for example dichloromethane;
7: in the presence of a suitable reducing agent, such as for example triacetoxyborohydride, and a suitable solvent, such as for example an alcohol, e.g. methanol.

It is considered to be within the knowledge of the person skilled in the art to recognize in which condition and on which part of the molecule a protective group may be appropriate. For instance, protective group on the $R_1$ substituent or on the pyrrazole moiety, or protective group on the $R_3$ substituent or on the $R_{2a,b,c}$ substituent or combinations thereof. The skilled person is also considered to be able to recognize the most feasible protective group, such as for example —C(=O)—O—$C_{1-4}$alkyl or

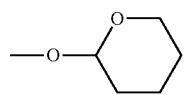

or O—Si(CH$_3$)$_2$(C(CH$_3$)$_3$) or —CH$_2$—O—CH$_2$CH$_2$—O—CH$_3$.

The present invention also comprises deuterated compounds. These deuterated compounds may be prepared by using the appropriate deuterated intermediates during the synthesis process.

The compounds of formula (I) may also be converted into each other via art-known reactions or functional group transformations.

Compounds of formula (I) wherein $R_1$ represents hydrogen can be converted into a compound of formula (I) wherein $R_1$ represents $C_{1-6}$alkyl or hydroxy$C_{1-6}$alkyl, by reaction with $C_{1-6}$alkyl-W or hydroxy$C_{1-6}$alkyl-W, wherein W represents a suitable leaving group, such as for example halo, e.g. bromo and the like, in the presence of a suitable base, such as for example sodium hydride or potassium carbonate, and a suitable solvent, such as for example acetonitrile or N,N-dimethylformamide.

Compounds of formula (I) wherein $R_1$ represents hydrogen can also be converted into a compound of formula (I) wherein $R_1$ represents $C_{1-6}$alkyl-OH, by reaction with W—$C_{1-6}$alkyl-O—Si(CH$_3$)$_2$(C(CH$_3$)$_3$) in the presence of a suitable base, such as for example sodium hydride, and a suitable solvent, such as for example N,N-dimethylformamide, followed by a deprotection reaction of the silyl protecting group by art-known methods.

Compounds of formula (I) wherein $R_1$ represents hydrogen, can also be converted into a compound of formula (I) wherein $R_1$ represents ethyl substituted with —S(=O)$_2$—$C_{1-4}$alkyl, by reaction with $C_{1-4}$alkyl-vinylsulfone, in the presence of a suitable base, such as for example triethylamine, and a suitable solvent, such as for example an alcohol, e.g. methanol or by reaction with $C_{1-4}$alkyl-2-bromoethylsulfone in the presence of a suitable deprotonating agent, such as for example NaH, and a suitable solvent, such as for example dimethylformamide.

Compounds of formula (I) wherein $R_{2b}$ or $R_{2c}$ represents —OCH$_3$ can be converted into a compound of formula (I) wherein $R_{2b}$ or $R_{2c}$ represents —OH by reaction with boron tribromide in the presence of a suitable solvent, such as for example dichloromethane.

Compounds of formula (I) wherein $R_{2b}$ or $R_{2c}$ represents —OH can be converted into a compound of formula (I) wherein $R_{2b}$ or $R_{2c}$ represents —OCH$_3$ by reaction with methyl iodine in the presence of a suitable base, such as for example potassium carbonate, and a suitable solvent, such as for example N,N-dimethylformamide.

Intermediates of formula (II) can be prepared as described in WO2013/061074, WO2013/061077, WO2013/061080 and WO2014/174307.

A further aspect of the invention is a process for the preparation of a compound of formula (I) as defined herein, which process comprises:
(i) reacting a compound of formula (II) with formaldehyde in the presence of a suitable solvent, such as for example dioxane, N,N-dimethylformamide, N,N-dimethylacetamide, at a suitable temperature, such as a temperature ranging from room temperature to reflux;

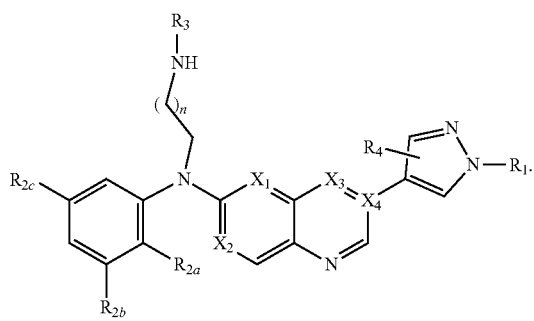

(II)

wherein the dotted line, $X_1$, $X_2$, $X_3$, $X_4$, $R_1$, $R_{2a}$, $R_{2b}$, $R_{2c}$, $R_3$, $R_4$ and n are as defined herein; and optionally thereafter converting one compound of the formula (I) into another compound of the formula (I).

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, esters, prodrugs, isotopes and protected forms thereof, for example, as discussed below; preferably, the ionic forms, or salts or tautomers or isomers or solvates thereof; and more preferably, the ionic forms, or salts or tautomers or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, esters, prodrugs, isotopes and protected forms thereof.

According to one aspect of the invention there is provided a compound as defined herein or a salt, tautomer, or solvate thereof. According to a further aspect of the invention there is provided a compound as defined herein or a salt or solvate thereof. References to compounds of the formula (I) and sub-groups thereof as defined herein include within their scope the salts or solvates or tautomers of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic, then a salt may be formed with a suitable cation. Examples of suitable inorganic cations include, but are not limited to, alkali metal ions such as Na⁺ and K⁺, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I). Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

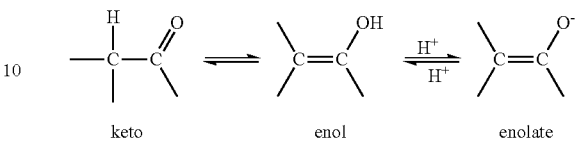

keto          enol          enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog (1966) *Angew. Chem. Int. Ed. Engl.*, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer). When a specific isomeric form is identified (e.g. S configuration, or E isomer), this means that said isomeric form is substantially free of the other isomer(s), i.e. said isomeric form is present in at least 55%, 60%, 65%, 70%, 75%, 80%, 85%, 90%, 95%, 99% or more (e.g. substantially all) of the total amount of the compound of the invention.

Whenever, hereinbefore or hereinafter, compounds include the following bond , this indicates that the compound is a single stereoisomer with unknown configuration or a mixture of stereoisomers.

The compounds of the invention include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a hydroxyl group. In another embodiment of the invention, formula (I) does not include within its scope esters of compounds of the formula (I) bearing a hydroxyl group. Examples of acyloxy (reverse ester) groups are represented by —OC(=O)R, wherein R is an acyloxy substituent, for example, a $C_{1-7}$ alkyl group, a $C_{3-20}$heterocyclyl group, or a $C_{5-20}$ aryl group, preferably a $C_{1-7}$ alkyl group. Particular examples of acyloxy groups include, but are not limited to, —OC(=O)CH3 (acetoxy), —OC(=O)CH$_2$CH$_3$, —OC(=O)C(CH$_3$)$_3$, —OC(=O)Ph, and —OC(=O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group is cleaved to yield the active drug. Such esters may be formed by esterification, for example, of any of the hydroxyl groups in the parent compound, with, where appropriate, prior protection of any other reactive groups present in the parent compound, followed by deprotection if required.

Examples of such metabolically labile esters include $C_{1-6}$aminoalkyl [e.g., aminoethyl; 2-(N,N-diethylamino) ethyl; 2-(4-morpholino)ethyl); and acyloxy-$C_{1-7}$alkyl [e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyll. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases (RTK) or upregulation of receptor tyrosine kinases may be particularly sensitive to the inhibitors. Patients with activating mutants of any of the isoforms of the specific RTKs discussed herein may also find treatment with RTK inhibitors particularly beneficial, for instance patients with tumors, e.g. bladder or brain tumors, with FGFR3-TACC3 translocation.

Vascular Endothelial Growth Factor Receptor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 µM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Examples of cancers which may be treated (or inhibited) include, but are not limited to, bladder cancer, urothelial cancer, metastatic urothelial cancer, surgically unresectable urothelial cancer, breast cancer, glioblastoma, lung cancer, non small cell lung cancer, squamous cell lung cancer, adenocarcinoma of the lung, pulmonary adenocarcinoma, small cell lung cancer, ovarian cancer, endometrial cancer, cervical cancer, soft tissue sarcoma, head and neck squamous cell carcinoma, gastric cancer, oesophageal cancer, squamous cell carcinoma of the oesophagus, adenocarcinoma of the oesophagus, cholangiocarcinoma, hepatocellular carcinoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used in the treatment of gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

A further subset of cancers includes hepatocellular cancer harboring FGF19 amplification or overexpression.

A subset of cancer includes cholangiocarcinoma, in particular cholangiocarcinoma with FGFR genomic alterations (fusions and/or mutations).

A subset of cancer includes advanced or refractory NSCLC, breast cancer, glioblastoma multiforme, urothelial cancer, ovarian cancer, head and neck cancer, oesophageal cancer, gastric cancer and cholangiocarcinoma, in particular advanced or refractory NSCLC, breast cancer, glioblastoma multiforme, urothelial cancer, ovarian cancer, head and neck cancer, oesophageal cancer, gastric cancer and cholangiocarcinoma with FGFR genomic alterations (fusions and/or mutations).

A subset of cancer includes metastatic or surgically unresectable urothelial cancer, in particular metastatic or surgically unresectable urothelial cancer with FGFR genomic alterations (fusions and/or mutations).

A subset of cancer includes cancer with FGFR genomic alterations (fusions and/or mutations).

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4;14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular, the compounds have activity against tumours with FGFR3-TACC3 translocation, in particular bladder or brain tumours with FGFR3-TACC3 translocation.

In particular the compounds are useful for the treatment of t(4;14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC (non small cell lung cancer), squamous cell carcinoma, liver cancer, kidney cancer, breast cancer, colon cancer, colorectal cancer, prostate cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target.

An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g. PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T6741 of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105.

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer. The compounds of the invention are particular useful in treatment of a patient having a FGFR3-TACC3 translocation.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetracarcin A;

glucocorticoids for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;
aromatase inhibitors such as exemestane, anastrozole, letrazole, testolactone and vorozole;
differentiating agents such as retinoids, vitamin D or retinoic acid and retinoic acid metabolism blocking agents (RAMBA) for example accutane;
DNA methyl transferase inhibitors for example azacytidine or decitabine;
antifolates for example premetrexed disodium;
antibiotics for example antinomycin D, bleomycin, mitomycin C, dactinomycin, carminomycin, daunomycin, levamisole, plicamycin, mithramycin;
antimetabolites for example clofarabine, aminopterin, cytosine arabinoside or methotrexate, azacitidine, cytarabine, floxuridine, pentostatin, thioguanine;
apoptosis inducing agents and antiangiogenic agents such as Bcl-2 inhibitors for example YC137, BH 312, ABT 737, gossypol, HA 14-1, TW 37 or decanoic acid;
tubuline-binding agents for example combrestatin, colchicines or nocodazole;
kinase inhibitors (e.g. EGFR (epithelial growth factor receptor) inhibitors, MTKI (multi target kinase inhibitors), mTOR inhibitors, cmet inhibitors) for example flavoperidol, imatinib mesylate, erlotinib, gefitinib, dasatinib, lapatinib, lapatinib ditosylate, sorafenib, sunitinib, sunitinib maleate, temsirolimus, 6-{difluoro [6-(1-methyl-1H-pyrazol-4-yl)[1,2,4]triazolo[4,3-b] pyridazin-3-yl]methyl}quinoline or a pharmaceutically ac ceptable salt thereof, 6-[difluoro(6-pyridin-4-yl[1,2, 4]triazolo[4,3-b]pyridazin-3-yl)methyl]quinoline or a pharmaceutically acceptable salt thereof;
farnesyltransferase inhibitors for example tipifarnib;
histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
Inhibitors of the ubiquitin-proteasome pathway for example PS-341, MLN 0.41 or bortezomib;
Yondelis;
Telomerase inhibitors for example telomestatin;
Matrix metalloproteinase inhibitors for example batimastat, marimastat, prinostat or metastat.
Recombinant interleukins for example aldesleukin, denileukin diftitox, interferon alfa 2a, interferon alfa 2b, peginterferon alfa 2b
MAPK inhibitors
Retinoids for example alitretinoin, bexarotene, tretinoin
Arsenic trioxide
Asparaginase
Steroids for example dromostanolone propionate, megestrol acetate, nandrolone (decanoate, phenpropionate), dexamethasone
Gonadotropin releasing hormone agonists or antagonists for example abarelix, goserelin acetate, histrelin acetate, leuprolide acetate
Thalidomide, lenalidomide
Mercaptopurine, mitotane, pamidronate, pegademase, pegaspargase, rasburicase
BH3 mimetics for example ABT-737
MEK inhibitors for example PD98059, AZD6244, CI-1040
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17alpha-hydroxylase-17,20-lyase inhibitor (CYP17), e.g. abiraterone, abiraterone acetate.

In one embodiment, the present invention relates to a combination of a compound of formula (I), a pharmaceutically acceptable salt thereof or a solvate thereof, or any sub-groups and examples thereof, and 6-{difluoro[6-(1-methyl-1H-pyrazol-4-yl)[1,2,4]triazolo[4,3-b]pyridazin-3-yl]methyl}quinoline or a pharmaceutically acceptable salt thereof.

In one embodiment, the present invention relates to a combination of a compound of formula (I), a pharmaceutically acceptable salt thereof or a solvate thereof, or any sub-groups and examples thereof, and 6-[difluoro(6-pyridin-4-yl[1,2,4]triazolo[4,3-b]pyridazin-3-yl)methyl]quinoline or a pharmaceutically acceptable salt thereof.

In one embodiment, the present invention relates to a pharmaceutical composition comprising a compound of formula (I), a pharmaceutically acceptable salt thereof or a solvate thereof, or any sub-groups and examples thereof, and 6-{difluoro[6-(1-methyl-1H-pyrazol-4-yl)[1,2,4]triazolo[4,3-b]pyridazin-3-yl]methyl}quinoline or a pharmaceutically acceptable salt thereof.

In one embodiment, the present invention relates to a pharmaceutical composition comprising a compound of formula (I), a pharmaceutically acceptable salt thereof or a solvate thereof, or any sub-groups and examples thereof, and 6-[difluoro(6-pyridin-4-yl[1,2,4]triazolo[4,3-b]pyridazin-3-yl)methyl]quinoline or a pharmaceutically acceptable salt thereof.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 mg/m2, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour *vinca* alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^3$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

Intermediates of formula (II) can be prepared as described in WO2013/061074, WO2013/061077, WO2013/061080 and WO2014/174307, which are incorporated herein by reference.

Experimental Part

Hereinafter, the term 'DCM' means dichloromethane, 'Me' means methyl, 'Et' means ethyl, 'MeOH' means methanol, 'Et$_2$O' means diethyl ether, 'EtOAc' means ethyl acetate, 'ACN' or 'CH$_3$CN' means acetonitrile, 'THF' means tetrahydrofuran, 'TFA' means trifluoroacetic acid, 'CO$_2$' means carbon dioxide, 'CH$_3$COONH$_4$' means ammonium acetate, 'MgSO$_4$' means magnesium sulfate, 'NH$_4$OH' means ammoniumhydroxide, 'K$_2$CO$_3$' means dipotassium carbonate, 'iPrNH$_2$' means isopropylamine, 'DMSO' means dimethyl sulfoxide, 'EDTA' means ethylenediaminetetraacetic acid, 'SFC' means supercritical fluid chromatography, 'MP' means melting point.

A. Preparation of Intermediates

Example A1

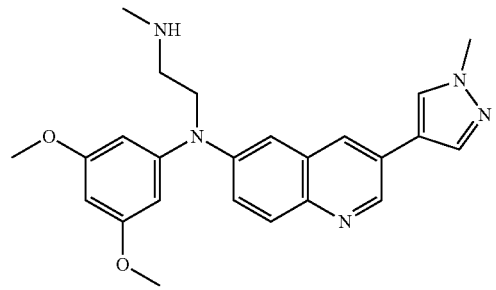 [SMILES: CNCCN(c1cc(OC)cc(OC)c1)c1ccc2ncc(-c3cnn(C)c3)cc2c1]

Preparation of Intermediate 1

In a tube, methylamine 2M in THF (18.6 ml; 37.3 mmol) was added, at room temperature, dropwise to a suspension of intermediate 11 of WO2013/061074 (1.8 g; 3.73 mmol), potassium carbonate (2.6 g; 18.7 mmol) in acetonitrile (30 mL). The tube was sealed and the mixture was heated at 80° C. overnight. The reaction mixture was cooled to room temperature and poured onto ice water. EtOAc was added and the organic layer was separated, washed with brine, dried over MgSO$_4$, filtered and the solvent was evaporated.

The crude (1.6 g) was purified by silica gel chromatography (Stationary phase: irregular SiOH 15-40 μm 80 g, Mobile phase: 92% DCM, 8% MeOH, 0.1% NH$_4$OH). The fractions containing the product were mixed and the solvent was evaporated to give 160 mg (10%) of intermediate 1.

B. Preparation of the Compounds of Formula (I)

Example B1

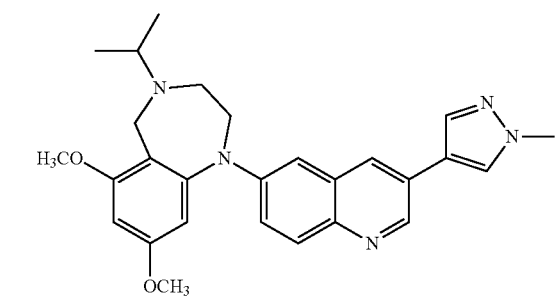 [SMILES: COc1cc(OC)c2c(c1)N(c1ccc3ncc(-c4cnn(C)c4)cc3c1)CCN(C(C)C)C2]

Preparation of compound 1

A solution of

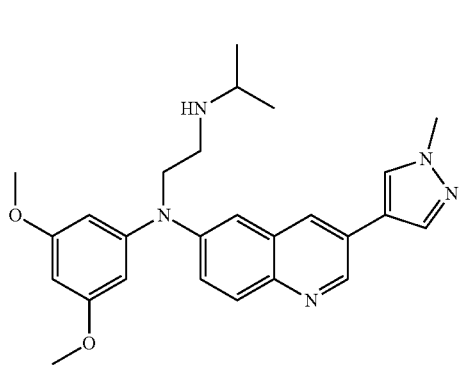 [SMILES: COc1cc(OC)cc(N(CCNC(C)C)c2ccc3ncc(-c4cnn(C)c4)cc3c2)c1]

(compound 1 of WO2013/061074) (32 mg; 0.072 mmol), formaldehyde (37% solution in water; 0.11 mL; 1.4 mmol) and dioxane (5 mL) was stirred at room temperature for 3 days. The solution was poured out into cooled water and the product was extracted with DCM. The organic layer was dried over MgSO$_4$, filtered and evaporated to dryness.

The crude (48 mg) was purified by silica gel chromatography (irregular bare silica 40 g, Mobile phase: 0.2% NH$_4$OH, 98% DCM, 2% MeOH). The fractions containing the product were mixed and concentrated to afford an intermediate fraction (20 mg) which was purified again by achiral SFC (Stationary phase: Chiralpak IA 5 µm 250*20 mm, Mobile phase: 55% CO$_2$, 45% MeOH (0.3% iPrNH$_2$)). The pure fractions were mixed, concentrated and freeze-dried with acetonitrile/water (20/80) to give 16 mg (49%; yellow powder) of compound 1. M.P.=80° C. (gummed).

Other compounds were prepared according to the above protocol of example 1. For instance, compound 2

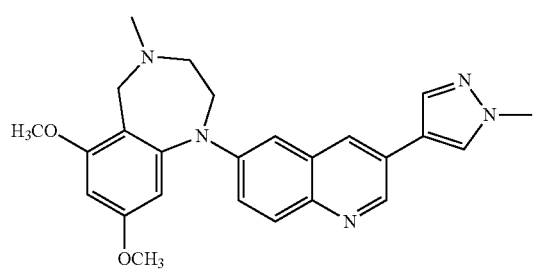

Starting intermediate intermediate 1

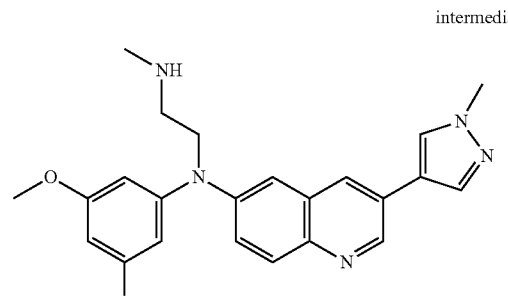

described herein compound 3

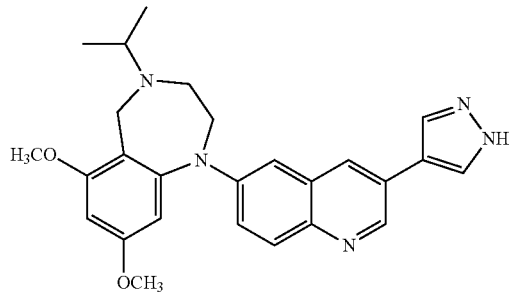

Starting intermediate (compound 22

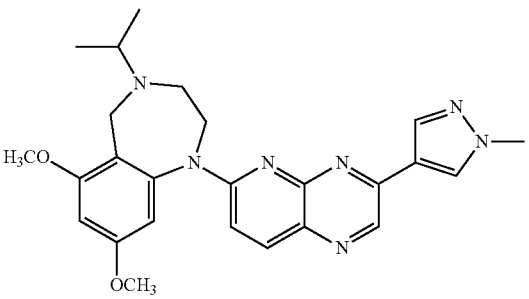

of WO2013/061074 wherein the tetrahydropyrane ring was removed after cyclization by reaction in methanol as a solvent with hydrochloric acid in methanol. (This reaction can also be performed with hydrochloric acid in dioxane, in a suitable sonvent, such as for example tetrahydrofuran.)

compound 7

Starting intermediate (compound 1

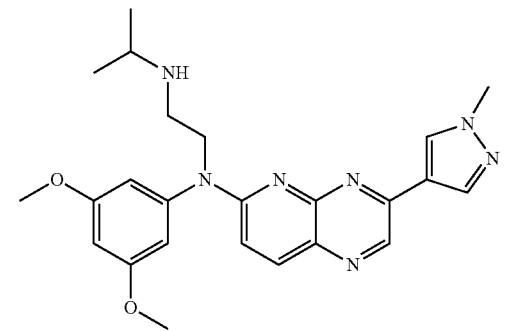

of WO2013/061080)

compound 9
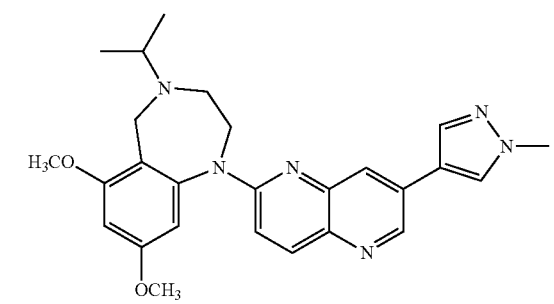
Starting intermediate
(compound 4
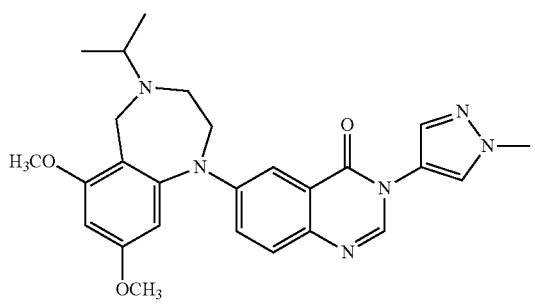
of WO2013/061077)
compound 11
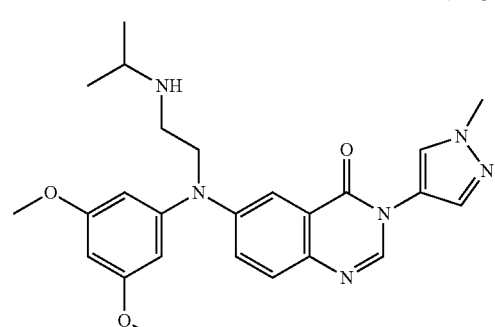
Starting intermediate
(compound 9
of WO2014/174307)
compound 12
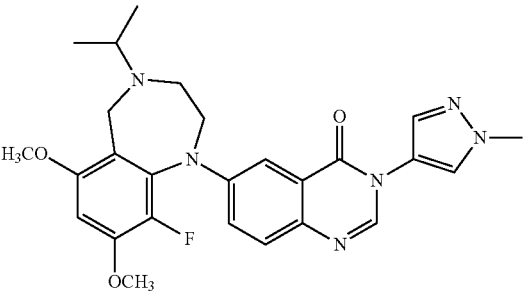
(compound 17
of WO2014/174307)
The following compound is prepared as follows:
Compound 13
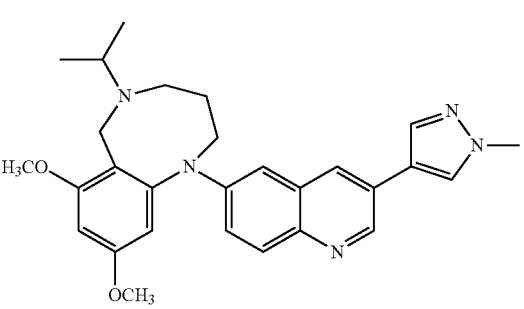 [SMILES: COc1cc(OC)c2c(c1)N(c1ccc3ncc(-c4cnn(C)c4)cc3c1)CCCN(C(C)C)C2]
is prepared from
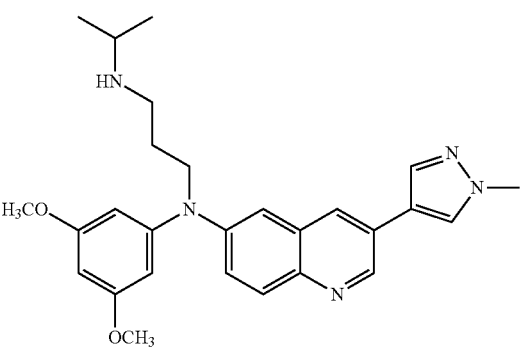 [SMILES: COc1cc(OC)cc(N(CCCNC(C)C)c2ccc3ncc(-c4cnn(C)c4)cc3c2)c1]
This intermediate is prepared from compound 4 of WO2013/061074 according to the protocol as described for compound 1 in WO2013/061074.

Example B2

Preparation of compound 4

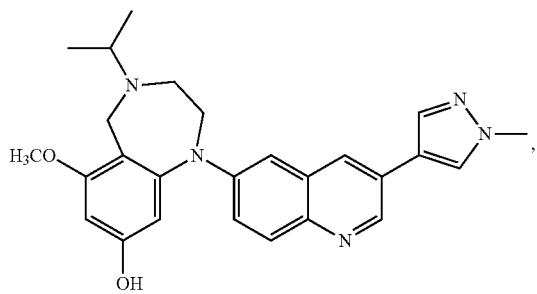 [SMILES: COc1cc(O)cc2c1CN(C(C)C)CCN2c1ccc2ncc(-c3cnn(C)c3)cc2c1]

compound

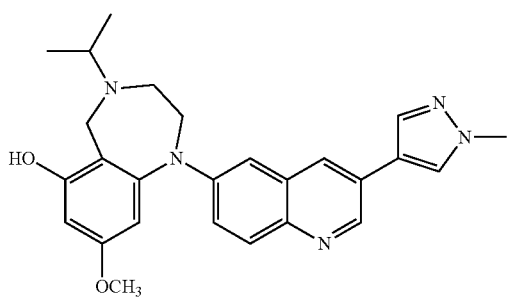 [SMILES: COc1cc(O)c2c(c1)N(c1ccc3ncc(-c4cnn(C)c4)cc3c1)CCN(C(C)C)C2]

and compound 6

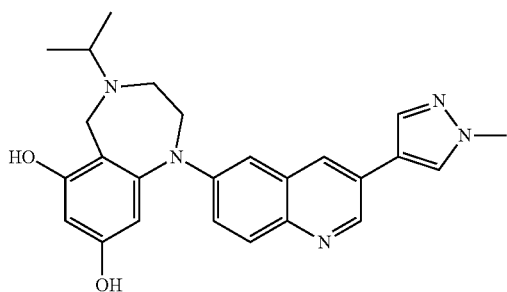 [SMILES: CC(C)N1CCN(c2ccc3ncc(-c4cnn(C)c4)cc3c2)c2cc(O)cc(O)c2C1]

The reaction was performed 5 times on different quantities (total: 1.05 g; 2.21 mmol; 96% pure):

The above compounds were prepared by adding 1M solution of boron tribromide in DCM (6.3 mL; 6.316 mmol) at 5° C. to a solution of compound 1 (500 mg; 1.053 mmol; 96% pure) in DCM (40 mL). The solution was allowed to warm up to room temperature and stirred for 1.5 hours. The reaction mixture was diluted with DCM, quenched with MeOH (15 mL) and evaporated to dryness. The residues were combined and purified by reverse phase chromatography (Gemini 150*25, 5µ; mobile phase: gradient from 20% $CH_3CN$, 80% $NH_4OH$ (0.05% aq) to 50% $CH_3CN$, 50% $NH_4OH$ (0.05% aq). The pure fractions were collected and the solvent was evaporated under vaccum. The aqueous layer was lyophilized yielding 200 mg of compound 6 (21%), 14 mg of compound 5 (3%) and 20 mg of compound 4 (2%).

Example B3

Compound 8

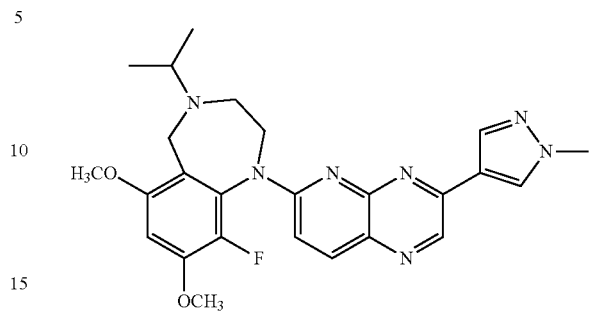

and compound 10

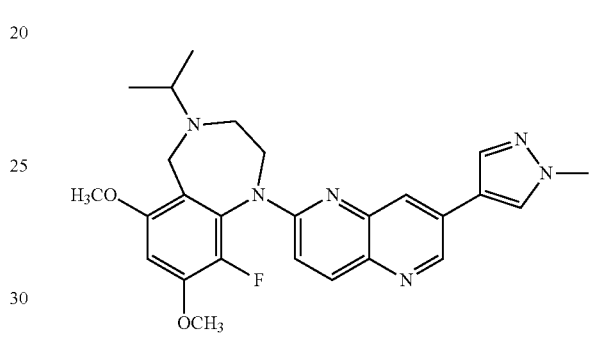

are prepared according to the method reported in scheme 2 hereinabove.

Analytical Part

LCMS (Liquid Chromatography/Mass Spectrometry) (See Table Below)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, CO, the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

Table of methods: LCMS Method codes (Flow expressed in mL/min; column temperature (T) in ° C.; Run time in minutes).

| | Instrument | Column | Mobile phase | gradient | Flow Column T | Run time |
|---|---|---|---|---|---|---|
| Method 1 | Waters: Acquity UPLC ® - DAD and Quattro MicroTM | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 minutes, to 10.5% A in 2.18 minutes, held for 1.94 minutes, back to 84.2% A in 0.73 minutes, held for 0.73 minutes. | 0.343 40 | 6.2 |
| Method 2 | Agilent 1200 equip with MSD 6110 | Phenomenex Luna-C18, 50 × 2 mm, 5 μm | A: H$_2$O (0.1% TFA) B: CH$_3$CN (0.05% TFA) | 90% A for 0.8 minutes, to 80% A in 3.7 minutes, held for 3 minutes, back to 90% A in 2 minutes, held for 0.5 minutes | 0.8 50 | 10 |

Melting Points

For a number of compounds, melting points (MP) were determined with a DSC1 (Mettler-Toledo). Melting points were measured with a temperature gradient of 10° C./minute. Maximum temperature was 300° C. Values are peak values.

For a number of compounds, melting points were obtained with a Kofler hot bench, consisting of a heated plate with linear temperature gradient, a sliding pointer and a temperature scale in degrees Celsius.

For a number of compounds, melting points were obtained with an automatic Melting Point Apparatus WRS-2A.

NMR

NMR experiment was carried out using a Bruker Avance 500 spectrometer equipped with a reverse triple-resonance ($^1$H, $^{13}$C, $^{15}$N TXI) probe head with z gradients and operating at 500 MHz for the proton and 125 MHz for carbon.

TABLE A1

Co. No. means compound number; Retention time (R$_t$) in minutes; MP means melting point (° C.).

| Co. No. | Compound | MP | Method: Kofler (K) | R$_t$ | [M + H]$^+$ | LCMS method |
|---|---|---|---|---|---|---|
| 1 | | 80° C. | K | 2.39 | 458 | Method 1 |
| 2 | | 199° C. | DSC | 2.17 | 430 | Method 1 |

TABLE A1-continued

Co. No. means compound number; Retention time (R$_t$) in minutes; MP means melting point (° C.).

| Co. No. | Compound | MP | Method: Kofler (K) | R$_t$ | [M + H]$^+$ | LCMS method |
|---|---|---|---|---|---|---|
| 3 | (structure) | 126° C. | K | 2.25 | 444 | Method 1 |
| 4 | (structure) | — | — | 2.10 | 444 | Method 2 |
| 5 | (structure) | — | — | 2.20 | 444 | Method 2 |
| 6 | (structure) | — | — | 1.89 | 430 | Method 2 |
| 7 | (structure) | 186 | DSC | 2.34 | 460 | Method 1 |

TABLE A1-continued

Co. No. means compound number; Retention time ($R_t$) in minutes; MP means melting point (° C.).

| Co. No. | Compound | MP | Method: Kofler (K) | $R_t$ | [M + H]$^+$ | LCMS method |
|---|---|---|---|---|---|---|
| 9 | (structure) | — | — | 2.55 | 459 | Method 2 |
| 11 | (structure) | >250 | WRS-2A | 2.64 | 475 | Method 2 |
| 12 | (structure) | >250 | WRS-2A | 2.58 | 493 | Method 2 |

As understood by a person skilled in the art, compounds synthesized using the protocols as indicated may exist as a solvate e.g. hydrate, and/or contain residual solvent or minor impurities.

Compound 1

$^1$H NMR (500 MHz, DMSO-d$_6$) δ ppm 8.83 (d, J=2.2 Hz, 1H) 8.32 (s, 1H) 8.15 (d, J=1.9 Hz, 1H) 8.03 (s, 1H) 7.74 (d, J=9.5 Hz, 1H) 7.22 (dd, J=9.3, 2.0 Hz, 1H) 6.91 (br s, 1H) 6.52 (d, J=2.2 Hz, 1H) 6.38 (d, J=2.5 Hz, 1H) 3.36-3.96 (m, 13H) 2.74-2.88 (m, 3H) 0.96 (d, J=6.6 Hz, 6H)

Pharmacological Part

Biological Assays A

FGFR1 (Enzymatic Assay)

In a final reaction volume of 30 μL, FGFR1 (h) (25 ng/ml) is incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 μM ATP in the presence of compound (1% DMSO final). After incubation for 60 minutes at room temperature the reaction is stopped with 2.27 nM EU-anti P-Tyr, 7 mM EDTA, 31.25 nM SA-XL-665 and 0.02% BSA which is present for 60 minutes at room temperature. Time-Resolved Fluorescence Resonance Energy Transfer (TR-FRET) signal (ex340 nm. Em 620 nm, em 655 nm) is measured afterwards and results are expressed in RFU (Relative Fluorescence Units). In this assay, the inhibitory effect of different compound concentrations (range 10 μM to 0.1 nM) is determined and used to calculate an IC$_{50}$ (M) and pIC$_{50}$ (−log IC$_{50}$) value.

FGFR2 (Enzymatic Assay)

In a final reaction volume of 30 μL, FGFR2 (h) (150 ng/ml) is incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 0.4 μM ATP in the presence of compound (1% DMSO final). After incubation for 60 minutes at room temperature the reaction is stopped with 2.27 nM EU-anti P-Tyr, 7 mM EDTA, 31.25 nM SA-XL-665 and 0.02% BSA which is present for 60 minutes at room temperature. Time-Resolved Fluorescence Resonance Energy Transfer (TR-FRET) signal (ex340 nm. Em 620 nm, em 655 nm) is measured afterwards and results are expressed in (Relative Fluorescence Units). In this assay, the inhibitory effect of different compound concentrations (range 10 µM to 0.1 nM) is determined and used to calculate an $IC_{50}$ (M) and $pIC_{50}$ ($-log\ IC_{50}$) value.

FGFR3 (Enzymatic Assay)

In a final reaction volume of 30 µL, FGFR3 (h) (40 ng/ml) is incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 25 µM ATP in the presence of compound (1% DMSO final). After incubation for 60 minutes at room temperature the reaction is stopped with 2.27 nM EU-anti P-Tyr, 7 mM EDTA, 31.25 nM SA-XL-665 and 0.02% BSA which is present for 60 minutes at room temperature. Time-Resolved Fluorescence Resonance Energy Transfer (TR-FRET) signal (ex340 nm. Em 620 nm, em 655 nm) is measured afterwards and results are expressed in RFU (Relative Fluorescence Units). In this assay, the inhibitory effect of different compound concentrations (range 10 µM to 0.1 nM) is determined and used to calculate an $IC_{50}$ (M) and $pIC_{50}$ ($-log\ IC_{50}$) value.

FGFR4 (Enzymatic Assay)

In a final reaction volume of 30 µL, FGFR4 (h) (60 ng/ml) is incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 µM ATP in the presence of compound (1% DMSO final). After incubation for 60 minutes at room temperature the reaction is stopped with 2.27 nM EU-anti P-Tyr, 7 mM EDTA, 31.25 nM SA-XL-665 and 0.02% BSA which is present for 60 minutes at room temperature. Time-Resolved Fluorescence Resonance Energy Transfer (TR-FRET) signal (ex340 nm. Em 620 nm, em 655 nm) is measured afterwards and results are expressed in RFU (Relative Fluorescence Units). In this assay, the inhibitory effect of different compound concentrations (range 10 µM to 0.1 nM) is determined and used to calculate an $IC_{50}$ (M) and $pIC_{50}$ ($-log\ IC_{50}$) value.

KDR (VEGFR2) (Enzymatic Assay)

In a final reaction volume of 30 µL, KDR (h) (150 ng/ml) is incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 3 µM ATP in the presence of compound (1% DMSO final). After incubation for 120 minutes at room temperature the reaction is stopped with 2.27 nM EU-anti P-Tyr, 7 mM EDTA, 31.25 nM SA-XL-665 and 0.02% BSA which is present for 60 minutes at room temperature. Time-Resolved Fluorescence Resonance Energy Transfer (TR-FRET) signal (ex340 nm. Em 620 nm, em 655 nm) is measured afterwards and results are expressed in RFU (Relative Fluorescence Units). In this assay, the inhibitory effect of different compound concentrations (range 10 µM to 0.1 nM) is determined and used to calculate an IC50 (M) and $pIC_{50}$ ($-log\ IC_{50}$) value.

Ba/F3-FGFR1 (Minus IL3 or Plus IL3) (Cellular Proliferation Assay)

In a 384 well plate, 100 nl of compound dilution in DMSO is sprayed before adding 50 µl cell culture medium (phenol red free RPMI-1640, 10% FBS, 2 mM L-Glutamine and 50 µg/ml Gentamycin) containing 20000 cells per well of Ba/F3-FGFR1-transfected cells. Cells are put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) is added to the wells, incubated for 4 hours at 37° C. and 5% $CO_2$ before RFU's (Relative Fluorescence Units) (ex. 540 nm., em. 590 nm.) are measured in a flurorescence plate reader.

In this assay, the inhibitory effect of different compound concentrations (range 10 µM to 0.1 nM) is determined and used to calculate an $IC_{50}$ (M) and $pIC_{50}$ ($-log\ IC_{50}$) value. As a counterscreen the same experiment is performed in the presence of 10 ng/ml murine IL3.

Ba/F3-FGFR3 (Minus IL3 or Plus IL3) (Cellular Proliferation Assay)

In a 384 well plate, 100 nl of compound dilution in DMSO is sprayed before adding 50 µl cell culture medium (phenol red free RPMI-1640, 10% FBS, 2 mM L-Glutamine and 50 µg/ml Gentamycin) containing 20000 cells per well of Ba/F3-FGFR3-transfected cells. Cells are put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) is added to the wells, incubated for 4 hours at 37° C. and 5% $CO_2$ before RFU's (Relative Fluorescence Units) (ex. 540 nm., em. 590 nm.) are measured in a flurorescence plate reader.

In this assay, the inhibitory effect of different compound concentrations (range 10 µM to 0.1 nM) is determined and used to calculate an $IC_{50}$ (M) and $pIC_{50}$ ($-log\ IC_{50}$) value. As a counterscreen the same experiment is performed in the presence of 10 ng/ml murine IL3.

Ba/F3-KDR (Minus IL3 or Plus IL3) (Cellular Proliferation Assay)

In a 384 well plate, 100 nl of compound dilution in DMSO is sprayed before adding 50 µl cell culture medium (phenol red free RPMI-1640, 10% FBS, 2 mM L-Glutamine and 50 µg/ml Gentamycin) containing 20000 cells per well of Ba/F3-KDR-transfected cells. Cells are put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) is added to the wells, incubated for 4 hours at 37° C. and 5% $CO_2$ before RFU's (Relative Fluorescence Units) (ex. 540 nm., em. 590 nm.) are measured in a flurorescence plate reader.

In this assay, the inhibitory effect of different compound concentrations (range 10 µM to 0.1 nM) is determined and used to calculate an $IC_{50}$ (M) and $pIC_{50}$ ($-log\ IC_{50}$) value.

As a counterscreen the same experiment is performed in the presence of 10 ng/ml murine IL3.

Ba/F3-FGFR4 (Cellular Proliferation Assay)

In a 384 well plate, 100 nl of compound dilution in DMSO is sprayed before adding 50 µl cell culture medium (phenol red free RPMI-1640, 10% FBS, 2 mM L-Glutamine and 50 µg/ml Gentamycin) containing 20000 cells per well of Ba/F3-FGFR4-transfected cells. Cells are put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) is added to the wells, incubated for 4 hours at 37° C. and 5% $CO_2$ before RFU's (Relative Fluorescence Units) (ex. 540 nm., em. 590 nm.) are measured in a flurorescence plate reader.

In this assay, the inhibitory effect of different compound concentrations (range 10 µM to 0.1 nM) is determined and used to calculate an $IC_{50}$ (M) and $pIC_{50}$ ($-log\ IC_{50}$) value.

Biological Assays B

Enzyme Binding Assays (KINOMEscan®)

Kinase enzyme binding affinities of compounds disclosed herein were determined using the KINOMEscan® technology performed by DiscoveRx Corporation, San Diego, Calif., USA (www.kinomescan.com). Table A2 reports the obtained pKd values, with Kd (M) being the inhibitor binding constant value and with pKd being −log Kd:

TABLE A2

| Compound | pKd FGFR1 | pKd FGFR2 | pKd FGFR3 | pKd FGFR4 | pKd VEGFR2 |
|---|---|---|---|---|---|
| 1 | 5.85 | 5.73 | 5.89 | 5.61 | <5.52 |
| 2 | 5.94 | <5.52 | 5.62 | <5.52 | <5.52 |
| 3 | 6.48 | 6.05 | 6.27 | 5.86 | <5.52 |
| 4 | <5.52 | <5.52 | <5.52 | <5.52 | <5.52 |
| 5 | 5.71 | <5.52 | 5.9 | <5.52 | <5.52 |
| 6 | <5.52 | <5.52 | <5.52 | <5.52 | <5.52 |
| 7 | <5.52 | <6 | <5.52 | <5.52 | 6.57 |
| 9 | 6.85 | 6.03 | 6.53 | 6.72 | 5.98 |
| 11 | <5.52 | <5.52 | <5.52 | <5.52 | <5.52 |
| 12 | 5.8 | 5.73 | 5.69 | <5.52 | <5.52 |

We claim:

1. A compound of formula (1)

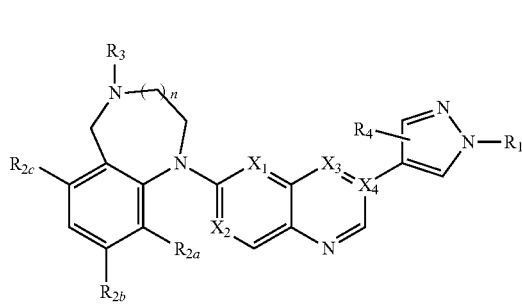

(I)

or a tautomeric or stereochemically isomeric form thereof, wherein $X_1$ is CH, $X_2$ is CH; $X_3$ is CH and $X_4$ is C (a);
$X_1$ is N, $X_2$ is CH, $X_3$ is N and $X_4$ is C (b); or
$X_1$ is CH, $X_2$ is CH, $X_3$ is C(=O) and $X_4$ is N;
and wherein the dotted line represents a bond in case of (a), and (b) and wherein the dotted line is absent in case of;
n represents an integer equal to 1 or 2;
$R_1$ represents hydrogen, $C_{1-6}$alkyl, hydroxy$C_{1-6}$alkyl, $C_{1-6}$alkyl substituted with —C(=O)NHCH$_3$, or $C_{1-6}$alkyl substituted with —S(=O)$_2$-$C_{1-4}$alkyl;
$R_{2a}$ represents hydrogen, fluoro or chloro;
$R_{2b}$ represents methoxy or hydroxyl;
$R_{2c}$ represents methoxy or hydroxyl;
$R_3$ represents hydrogen, $C_{1-6}$alkyl, $C_{3-6}$ cycloalkyl, or $C_{1-2}$alkyl substituted with $C_{3-6}$cycloalkyl;
$R_4$ represents hydrogen, methyl or ethyl;
or a pharmaceutically acceptable salt or solvate thereof.

2. The compound according to claim 1, wherein the compound has the following structure

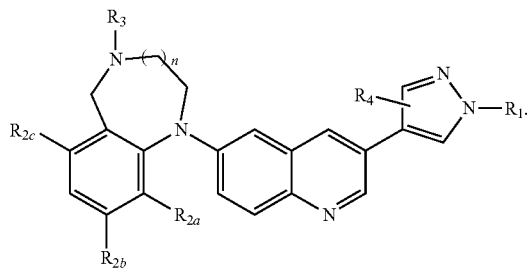

(Ia)

3. The compound according to claim 1, herein the compound has the following structure

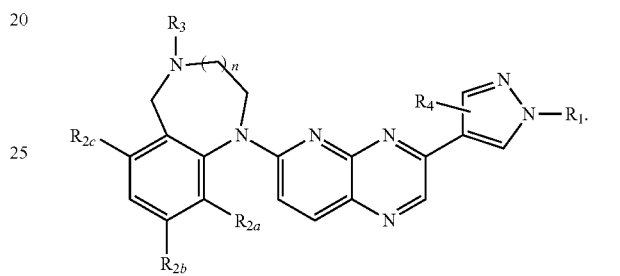

(Ib)

4. The compound according to claim 1, wherein the compound has the following structure

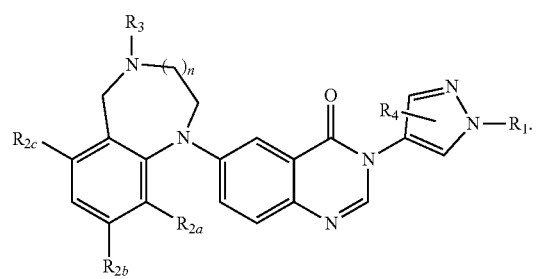

(Ic)

5. The compound according to claim 1 wherein n represents an integer equal to 1.

6. The compound according to claim 1 wherein $R_1$ represents hydrogen or $C_{1-6}$alkyl.

7. The compound according to claim 6 wherein $R_1$ represents hydrogen or $C_{1-4}$alkyl.

8. The compound according to claim 1 wherein $R_{2a}$ represents hydrogen or fluoro.

9. The compound according to claim 8 wherein $R_{2a}$ represents fluoro.

10. The compound according to claim 1 wherein $R_{2b}$, represents methoxy.

11. The compound according to claim 1 wherein $R_{2c}$ represents methoxy.

12. The compound according to claim 1 wherein $R_3$ represents $C_{1-6}$alkyl.

13. The compound according to claim 1 wherein $R_4$ represents hydrogen.

14. The compound according to claim 1 wherein the compound is

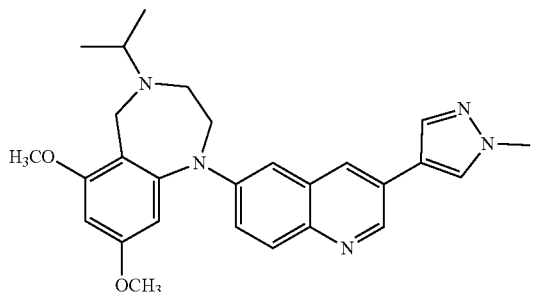

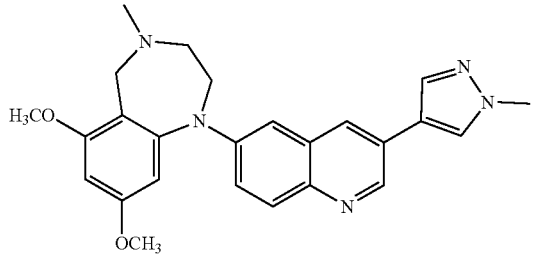

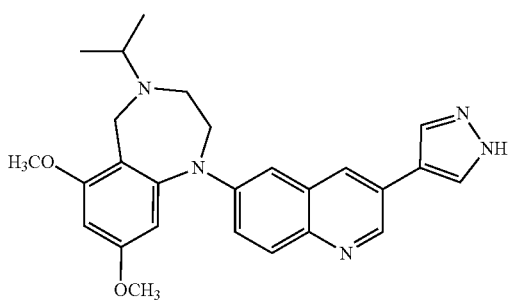

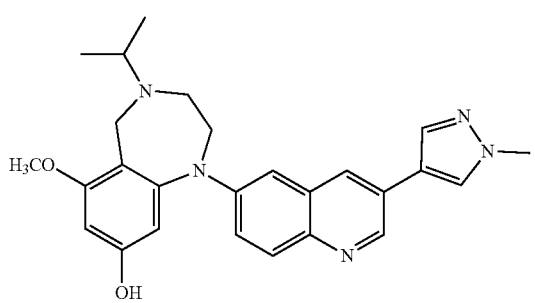

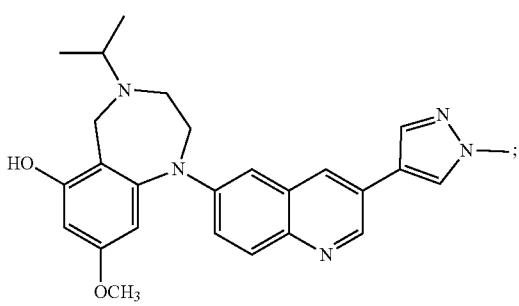

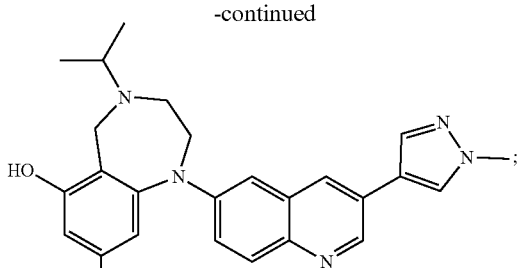

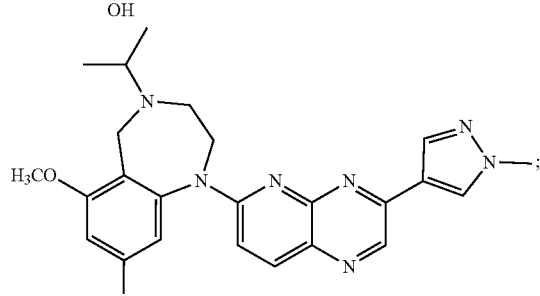

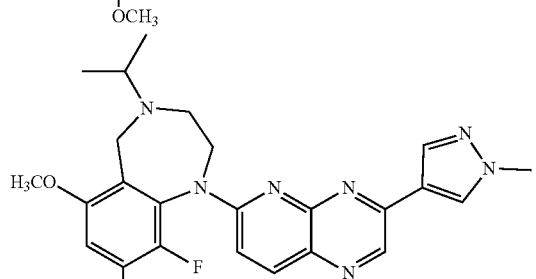

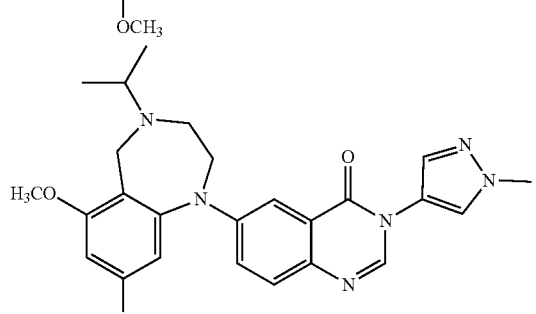

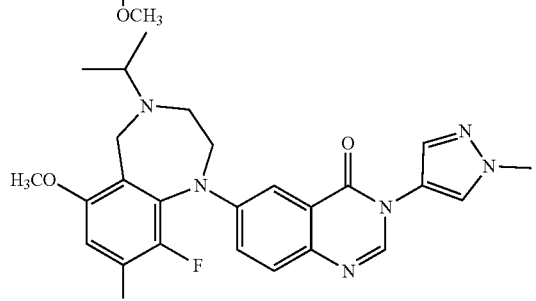

or a pharmaceutically acceptable salt or solvate thereof.

15. A pharmaceutical composition comprising a compound of claim 1.

16. A method of treating a disease state or condition mediated by a FGFR kinase comprising administering a compound as defined in claim 1.

17. A method of treating bladder cancer comprising administering a compound as defined in claim 1.

18. A method for treating a disease state or condition mediated by a FGFR kinase, which method comprises administering to a subject in need thereof a compound as defined in claim 1.

19. A method for the treatment of bladder cancer, which method comprises administering to a subject in need thereof a compound as defined in claim 1.

20. A method of treating urothelial cancer comprising administering a compound as defined in claim 1.

21. The method of claim 20, wherein the urothelial cancer is surgically unresectable urothelial cancer.

22. The method of claim 20, wherein the urothelial cancer is metastatic urothelial cancer.

23. A method for the treatment of urothelial cancer, which method comprises administering to a subject in need thereof a compound as defined in claim 1.

24. The method of claim 23, wherein the urothelial cancer is surgically unresectable urothelial cancer.

25. The method of claim 23, wherein the urothelial cancer is metastatic urothelial cancer.

\* \* \* \* \*